(12) United States Patent
Yin et al.

(10) Patent No.: US 12,270,024 B2
(45) Date of Patent: Apr. 8, 2025

(54) ENGINEERED MICROORGANISMS EXPRESSING ACETOACETYL-COA REDUCTASE VARIANTS AND METHODS FOR INCREASING PROPORTION OF 3-HYDROXYHEXANOIC ACID IN PHA

(71) Applicant: SHENZHEN BLUEPHA BIOSCIENCES CO., LTD., Guangdong (CN)

(72) Inventors: Jin Yin, Guangdong (CN); Yu Wang, Guangdong (CN); Jiajia Li, Guangdong (CN); Jie Hou, Guangdong (CN); Liang Zou, Guangdong (CN); Zixian Chen, Guangdong (CN)

(73) Assignee: SHENZHEN BLUEPHA BIOSCIENCES CO., LTD., Guangdong (CN)

( * ) Notice: Subject to any disclaimer, the term of this patent is extended or adjusted under 35 U.S.C. 154(b) by 0 days.

(21) Appl. No.: 18/031,556

(22) PCT Filed: Jun. 28, 2022

(86) PCT No.: PCT/CN2022/101796
§ 371 (c)(1),
(2) Date: Apr. 12, 2023

(87) PCT Pub. No.: WO2023/193352
PCT Pub. Date: Oct. 12, 2023

(65) Prior Publication Data
US 2024/0263130 A1 Aug. 8, 2024

(30) Foreign Application Priority Data
Apr. 6, 2022 (CN) .................. 202210353444.8

(51) Int. Cl.
*C12N 1/20* (2006.01)
*C12N 9/04* (2006.01)
(Continued)

(52) U.S. Cl.
CPC .............. *C12N 1/20* (2013.01); *C12N 9/0006* (2013.01); *C12N 9/1029* (2013.01); *C12N 9/88* (2013.01);
(Continued)

(58) Field of Classification Search
CPC ...... C12N 1/20; C12N 9/0006; C12N 9/1029; C12N 9/88; C12N 15/74; C12N 15/90;
(Continued)

(56) References Cited

U.S. PATENT DOCUMENTS 7,384,766 B2 * 6/2008 Maruyama ............. C12N 15/52
435/69.1

FOREIGN PATENT DOCUMENTS

| CN | 107418960 A | 12/2017 |
| CN | 110079489 A | 8/2019 |

(Continued)

OTHER PUBLICATIONS

UniProt ID A0A0D1V245_VIBPH (https://www.uniprot.org/uniprotkb/A0A0D1V245/entry) (Year: 2015).*
(Continued)

*Primary Examiner* — Louise W Humphrey
*Assistant Examiner* — Rachel Emily Martin
(74) *Attorney, Agent, or Firm* — Mendelsohn Dunleavy P.C.

(57) ABSTRACT

The present invention relates to the technical field of microorganisms, and specifically to engineered microorganisms expressing acetoacetyl-CoA reductase variants and methods for increasing the proportion of 3-hydroxyhexanoic acid in PHA. The acetoacetyl-CoA reductase variants and their
(Continued)

coding genes provided by the present invention can significantly increase the proportion of 3-hydroxyhexanoic acid in PHA produced by strains; the proportion of 3-hydroxyhexanoic acid in PHA produced by the engineered *Ralstonia eutropha* constructed utilizing the acetoacetyl-CoA reductase variants and their coding genes provided by the present invention is significantly increased, which provides new genes and strain resources for strains producing poly (3-hydroxybutyrate-co-3-10 the development of engineered hydroxyhexanoate) with high proportion of 3-hydroxyhexanoic acid.

12 Claims, 3 Drawing Sheets

Specification includes a Sequence Listing.

(51) Int. Cl.
  *C12N 9/10*    (2006.01)
  *C12N 9/88*    (2006.01)
  *C12N 15/74*   (2006.01)
  *C12N 15/90*   (2006.01)
  *C12P 7/625*   (2022.01)
  *C12R 1/01*    (2006.01)

(52) U.S. Cl.
  CPC .............. *C12N 15/74* (2013.01); *C12N 15/90* (2013.01); *C12P 7/625* (2013.01); *C12N 2510/00* (2013.01); *C12R 2001/01* (2021.05); *C12Y 101/01036* (2013.01); *C12Y 402/01119* (2013.01)

(58) Field of Classification Search
  CPC . C12N 2510/00; C12P 7/625; C12R 2001/01; C12Y 101/01036; C12Y 402/01119
  See application file for complete search history.

(56) References Cited

FOREIGN PATENT DOCUMENTS

| CN | 111615555 A | 9/2020 |
|---|---|---|
| CN | 112368385 A | 2/2021 |
| CN | 113583922 A | 11/2021 |
| CN | 114480318 A | 5/2022 |
| EP | 1700909 B1 | 8/2015 |
| JP | 2001-275675 A | 10/2001 |
| JP | 2007-228894 A | 9/2007 |
| KR | 10-0447535 B1 | 8/2004 |
| WO | 2004056960 A2 | 7/2004 |
| WO | 2011074842 A2 | 6/2011 |
| WO | 2014047209 A1 | 3/2014 |
| WO | 2019142717 A1 | 7/2019 |

OTHER PUBLICATIONS

Hu, Chun-Keng, et al. "Enhancements in Ethanol Tolerance of a Self-flocculating Yeast by Calcium Ion Through Decrease in Plasmalemma Permeability." Chinese Journal of Biotechnology 19.6 (2003): 715-719.

Zhang, Mengxiao, et al. "Modification of acetoacetyl-CoA reduction step in Ralstonia eutropha for biosynthesis of poly (3-hydroxybutyrate-co-3-hydroxyhexanoate) from structurally unrelated compounds." Microbial Cell Factories 18.147 (2019): 1-12.

Orita, Izumi, et al. "Identification of mutation points in Cupriavidus necator NCIMB 11599 and genetic reconstitution of glucose-utilization ability in wild strain H16 for polyhydroxyalkanoate production." Journal of Bioscience and Bioengineering 113.1 (2012): 63-69.

National Center for Biotechnology Information, "acetoacetyl-CoA reductase [Lysobacter prati]" Accession No. WP_158733746.1, [retrieved Apr. 10, 2023]. <URL: https://www.ncbi.nlm.nih.gov/protein/WP_158733746> (2020): 1 pages.

Notice of Reasons for Refusal for corresponding Japanese application No. 2023-529891; dated May 7, 2024 (7 pages) Machine Translation.

First Office Action for corresponding Chinese application No. 202210353444.8; dated May 25, 2022 (29 pages) Machine Translation.

Partial Supplementary Search Report for corresponding European application No. 22871170.1; dated Oct. 30, 2023 (16 pages).

Extended European Search Report for corresponding European application No. 22871170.1; dated Jan. 30, 2024 (14 pages).

Genbank, "acetoacetyl-CoA reductase [Halomonas subterranea]" Accession No. WP_092827727 (2019): 1 page.

Genbank, "MAG: beta-ketoacyl-ACP reductase [Betaproteobacteria bacterium]" Accession No. TMH24977 (2019): 2 pages.

Genbank, "MAG: acetoacetyl-CoA reductase [*Rhizobacter* sp.]" Accession No. MBC7708888 (2021): 2 pages.

Genbank, "acetoacetyl-CoA reductase [Neptunomonas japonica]" Accession No. WP_028470123 (2019): 1 page.

Genbank, "beta-ketoacyl-ACP reductase [Thauera aromatica]" Accession No. WP_107220394 (2019): 1 page.

Geneseq Online, "PHA production related acetoacetyl-CoA reductase variant, SEQ 9." Accession No. BLH02526 (2022): 1 page.

Geneseq Online, "Xanthomonas campestris acetoacetyl-CoA reductase" Accession No. BBE62016 (2014): 1 page.

Geneseq Online, "Chromobacterium violaceum phaB, role in polyhydroxyalkanoate synthesis." Accession No. ADQ26350 (2004): 1 page.

Chen XY, et al. "Thirty years of metabolic engineering for biosynthesis of polyhydroxyalkanoates." Chinese Journal of Biotechnology, 37.5 (2021): 1794-1811. (English Abstract).

Shaoping, Ouyang "Efficient fermentation production of new biomaterial 3-hydroxybutyric acid and 3-hydroxyhexanoic acid copolyester (PHBHHx)." Master's Thesis, Tsinghua University (2004): 1-4 (English Abstract).

Tan, Hua Tiang, et al. "Evaluation of BP-M-CPF4 polyhydroxyalkanoate (PHA) synthase on the production of poly (3-hydroxybutyrate-co-3-hydroxyhexanoate) from plant oil using Cupriavidus necator transformants." International Journal of Biological Macromolecules 159 (2020): 250-257.

Park, Si Jae, et al. "Production of Poly(3-hydroxybutyrate-co-3-hydroxyhexanoate) by Metabolically Engineered *Escherichia coli* Strains." Biomacromolecules 2.1 (2001): 248-254.

Olavarria, Karel, et al. "An NADH preferring acetoacetyl-CoA reductase is engaged in poly-3-hydroxybutyrate accumulation in *Escherichia coli*." Journal of Biotechnology 325 (2021): 207-216.

Zheng, Yang, et al. "Engineering biosynthesis of polyhydroxyalkanoates (PHA) for diversity and cost reduction." Metabolic Engineering 58 (2019): 82-93.

\* cited by examiner

Example 2. fermentation performance of the strains

Example 3. fermentation performance of the strains

Example 4. fermentation performance of the strains

SEQUENCE LISTING

<160> NUMBER OF SEQ ID NOS: 36

<210> SEQ ID NO 1
<211> LENGTH: 741
<212> TYPE: DNA
<213> ORGANISM: Artificial Sequence
<220> FEATURE:
<223> OTHER INFORMATION: acetoacetyl CoA reductase

<400> SEQUENCE: 1

```
atgcagagcc gcgtggccct ggtgaccggc ggcaccggcg gcatcggcac ctcgatcatc      60
cagcgcctgg cccagaccgg ccaccgcgtg gccaccaact accgcgacga ggaccgcgcg     120
cgcgcctggc aggagaagat gcgcgcggcc ggcgtggagg tggccctggc cccgggcgac     180
gtgtcgagcc cggagcaggc ccaggccctg gtggagcaga tccagcgcga cctgggcccg     240
atcgaggtgc tggtgaacaa cgccggcatc acccgcgact cgaccttcca ccgcatgacc     300
ccgctgcagt ggaacgaggt gatcggcacc aacctgaaca gctgcttcaa cgtgacccgc     360
ccggtgatcg agggcatgcg cgagcgcaag tggggccgca tcgtgcagat ctcgagcatc     420
aacggcctga gggccagta  cggccaggcc aactacgcgg ccgccaaggc gggcatgcac     480
ggcttcacca tcagcctggc ccgcgagaac gcccgcttcg gcgtgaccgt gaacaccgtg     540
tcgccgggct acgtggccac cgacatggtg atgagcgtgc cggaggaagt gcgcgcgaag     600
atcgtggcgg agatcccgac cggccgcctg gcacccccga acgagatcgc gtacgccgtg     660
tcgttcctgg tggcggagga agccgcctgg atcaccggca gcaacctgga catcaacggt     720
ggccaccaca tgggctggta a                                                741
```

<210> SEQ ID NO 2
<211> LENGTH: 741
<212> TYPE: DNA
<213> ORGANISM: Artificial Sequence
<220> FEATURE:
<223> OTHER INFORMATION: acetoacetyl-CoA reductase

<400> SEQUENCE: 2

```
atgcagaagc tggccctgat caccggcagc aagggcggca tcggctcggc catcaccgag      60
aagctggtgc aggacggctt ccgcatcatc gcgacctact tcaccggcaa ctacgagtgc     120
gccaaggagt ggttcgacga aagggcttc agcgaggacc aggtgaccct gttcgagctg     180
gacgtgaccg acgcggacag ctgccgcgag cgcctgacca gctgctggga gaacgagggc     240
accgtggacg tgctggtgaa caacgcgggc atcacccgcg actgcacctt caagcgcatg     300
accgccgagc agtggaacga cgtgatcaac accaacctga acagcgtgtt caacgtgacc     360
cagccgctgt tcgcggccat gtgcgagaag ggcggcggcc gcatcatcaa catctcgagc     420
gtgaacggcc tgaagggcca gttcggccag accaactact cggccgcgaa ggcgggcatg     480
atcggcttca gcaaggccct ggccttcgag ggcgcccgca gcggcgtgac cgtgaacgtg     540
gtggcccccg gctacaccgg caccccgatg gtgcaggcca tccgccagga cgtgctggac     600
agcatcatcg aaaccgtgcc gatgaagcgc ctggccaccc cggaggagat cgccagcgcc     660
gtggcctacc tggcctcgga cgccggcgcc tacatcaccg cgaaaccct  gagcgtgaac     720
ggcggcctgt acatgcagta a                                                741
```

<210> SEQ ID NO 3
<211> LENGTH: 816
<212> TYPE: DNA
<213> ORGANISM: Artificial Sequence

```
<220> FEATURE:
<223> OTHER INFORMATION: acetacetyl-CoA reductase

<400> SEQUENCE: 3
atgaccaccg ccgcggccga gaagcgcgcg gccaccaact cgggctcgga gccggtgcgc      60
gaggccgtgc cgccgctgaa gcagcgcatc gccttcgtgt cgggcggcat gggcggcatc     120
ggcagcgcgg tgtgccgtcg cctggtgcgc aacggcgccc gcgtggtggc gggctgcctg     180
ccgggctacg agaagaagga cgagtggatc gccaagatgc gcggcgaggg cctgcaggtg     240
cacgccgccg agggcgacgt ggacgactac gagtcgtgcg cggacatgtt ctaccagatc     300
ggcagcgtga tcgcccggt ggacatcctg gtgaacaacg ccggcatcac ccgcgacggc      360
atgttcaagc gcatgagccc ggccgactgg tacgccgtga tcaacaccaa cctgaacagc     420
gtgttcaacg tgacccgcca ggtgatcgag ggcatgatgg agcgcggctg gggccgcatc     480
atcaacatct cgagcgtgaa cgcgctgaag gccagttcg ccagaccaa ctacagcgcc       540 gccaaggcgg gcatgcacgg cttcagcaag gcgctggccc aggaagtggt gaagaagggc     600
gtgaccgtga acaccgtgtc gccgggctac gtggaaaccg acatggtgcg cgccatgaag     660
ccggaggtgc tgcagagcat cgtggagcag atcccgatgg ccgcttcgc ccagccggag      720 gagatcgcca gcctggtggc ctacctggcc tcggaggaag ccggctacat caccggcgcc     780
aacatctcga tcaacggcgg cctgcacatg gtgtaa                                816

<210> SEQ ID NO 4
<211> LENGTH: 747
<212> TYPE: DNA
<213> ORGANISM: Artificial Sequence
<220> FEATURE:
<223> OTHER INFORMATION: acetoacetyl-CoA reductase

<400> SEQUENCE: 4
atggcgaacc aggccccggt ggcctgggtg accggcggca ccggcggcat cggcaccgcc      60
atctgccgct cgctggcgga cgccggctac ctggtggtgg ccggctacca caacccggag     120
aaggccaaga cctggctggc cagccagcag gccgacggct acaacaacat cgccctgagc     180
ggcgtggacc tggcggacca ccaggcctgc ctgcaggggcg cccagcagat ccaggagcag     240
cacggcccga tctcggtgct ggtgaactgc gcgggcatca cccgcgacgg caccatgaag     300
aagatgagct acgagcagtg gtacgaggtg atcgacacca acctgaactc ggtgttcaac     360
acctgccgca gcgtgatcga gatgatgctg gagaacggct acggccgcat catcaacatc     420
tcgagcatca acgccgcaa gggccagttc ggccaggcca actacgcggc cgccaaggcc      480
ggcatgcacg gcctgaccat gtcgctggcc caggaaaccg cgaccaaggg catcaccgtg     540
aacaccgtga gccgggctac catcgccacc gacatgatca tgaacatccc ggagaaggtg     600
cgcgaggcca tccgcgaaac catcccggtg aagcgctacg gcaccccgga ggagatcggc     660
cgcctggtga ccttcatcgc cgacaaggag agcggcttca tcaccggcgc gaacttcgac     720
atcaacggtg gccagttcat gggctaa                                        747

<210> SEQ ID NO 5
<211> LENGTH: 741
<212> TYPE: DNA
<213> ORGANISM: Artificial Sequence
<220> FEATURE:
<223> OTHER INFORMATION: acetoacetyl-CoA reductase

<400> SEQUENCE: 5
```

| | |
|---|---|
| atgtcgcgcg tggccctggt gaccggcggc atgggcggcc tgggcgaggc gatctgcatc | 60 |
| aagatggcgg ccctgggcta ccaggtggtg accacctact cgccgggcaa caagacctgg | 120 |
| aaggagtggc tggacagcat gaacaagatg ggcttcggct cccgcgccta cccgtgcgac | 180 |
| gtggccgact acgacagcgc caccgcctgc gtggccctga tcgtgaagga agtgggcccg | 240 |
| gtggacgtgc tggtgaacaa cgcgggcatc acccgcgaca tgaccttcaa gaagatggac | 300 |
| aagatcaact gggacgccgt ggtggcgacc aacctggaca gcaccttcaa catgaccaag | 360 |
| caggtgtgcg acggcatgct ggagcgcggc tggggccgca tcgtgaacat ctcgtcggtg | 420 |
| aacggccaga agggcgcctt cggccagacc aactacagcg cggccaaggc cggcatgcac | 480 |
| ggcttcacca aggccctggc cctggaggtg gcccgcaagg gcgtgaccgt gaacaccatc | 540 |
| agcccgggct acatcggcac caagatggtg atggcgatcc cgtcggacgt gctggagagc | 600 |
| aagatcatcc cgcagatccc gatgggccgc tgggcaagc cggaggaagt ggcgggcctg | 660 |
| gtggcctacc tggccagcga cgaggcggcg ttcctgaccg cgccaacat cgcgatcaac | 720 |
| ggtggccagc acatgagcta a | 741 |

<210> SEQ ID NO 6
<211> LENGTH: 744
<212> TYPE: DNA
<213> ORGANISM: Artificial Sequence
<220> FEATURE:
<223> OTHER INFORMATION: acetoacetyl-CoA reductase

<400> SEQUENCE: 6

| | |
|---|---|
| atgacccagc gcatcgccat cgtgaccggc gccaacggcg gcctgggcga gagcatgtgc | 60 |
| aaggccctgg ccgagcaggg ccgcaaggtg gtgggcacct tcgtgccggg ccacgacgcg | 120 |
| gccgcggcca gctggcagga agagatgaag cagcagggct cgacatcac catgaaggcc | 180 |
| gtggacgtgt cggacttcaa cgactgcaag cgcctgctgg aggagatcga gtcgagcgag | 240 |
| ggcagcgtgg acatcctggt gaacaacgcg gcatcaccc gcgacgcgcc gctgaagaag | 300 |
| atgcagccgg agcagtggca ggcggtgatc ggcaccaacc tgaactcgat gttcaacatg | 360 |
| agccagccga tcttcgaggc catgtgcaac cgcggctggg gccgcatcgt gaacatctcg | 420 |
| agcctgaacg gcgagaaggg ccagttcggc caggccaact acagcgcggc caaggcgggc | 480 |
| atctacggct tcaccaaggc catcgcgcag gaaggcgcca gaagggcgt gaccgtgaac | 540 |
| tcggtgagcc cgggctacat cgacaccccg atggtgcgcc aggtgccgga gaacgtgctg | 600 |
| aacagcatcg tgggcggcat cccggtgggc cgcctgggcc agccgaggga gatcgcccgc | 660 |
| gcggtgtcgt tcctgaccgc ggacgacgcc ggcttcatca ccggcaccaa catcagcgtg | 720 |
| aacggtggcc agtacatggc gtaa | 744 |

<210> SEQ ID NO 7
<211> LENGTH: 741
<212> TYPE: DNA
<213> ORGANISM: Artificial Sequence
<220> FEATURE:
<223> OTHER INFORMATION: acetoacetyl-CoA reductase

<400> SEQUENCE: 7

| | |
|---|---|
| atgtcgcgcg tggccctggt gaccggcggc atgggcggcc tgggcgaggc gatctgcatc | 60 |
| aagctggccg cgctgggcta caaggtggtg accacccaca gcccgggcaa caccaaggcg | 120 |
| gccgagtggc tgctgaccat gaacaacatg ggctacggct tcaaggccta cccgtgcgac | 180 |
| gtgagcgact tcgactcgag caaggcgtgc gtggaaaccg tgacccgcga agtgggcccg | 240 |

| | | | |
|---|---|---|---|
| gtggacgtgc | tggtgaacaa | cgccggcatc acccgcgaca | tgaccttcaa gaagatgacc | 300 |
| aaggccgact | gggacgcggt | gatcggcacc aacctggact | cggtgttcaa catgaccaag | 360 |
| caggtgatgg | acggcatggt | ggagcgtcgc tggggccgcg | tgatcaacgt gtcgtcggtg | 420 |
| aacggccaga | agggcgcctt | cggccagacc aactactcgg | cggccaaggc cggcatgcac | 480 |
| ggcttcacca | aggccctggc | cctggaggtg gcccgcaacg | gcgtgaccgt gaacaccatc | 540 |
| tcgccgggct | acatcggcac | caagatggtg atggccatcc | gcaggagat cctggacagc | 600 |
| aagatcctgc | cgcagatccc | gctggcccgc ctgggcaagc | cggaggagat cgcgggcctg | 660 |
| gtggcctacc | tgagctcgga | ggaagccgcc ttcgtgaccg | cgcgaacat cagcatcaac | 720 |
| ggtggccagc | acatgttcta | a | | 741 |

<210> SEQ ID NO 8
<211> LENGTH: 2887
<212> TYPE: DNA
<213> ORGANISM: Artificial Sequence
<220> FEATURE:
<223> OTHER INFORMATION: phaC gene

<400> SEQUENCE: 8

| | | | |
|---|---|---|---|
| cgggcgtgcc | catgatgtag | agcaccagcg ccaccggcgc | catgccatac atcaggaagg | 60 |
| tgcaacgcc | tgccaccacg | ttgtgctcgg tgatcgccat | catcagcgcc acgtagagcc | 120 |
| agccaatggc | cacgatgtac | atcaaaaatt catccttctc | gcctatgctc tggggcctcg | 180 |
| gcagatgcga | gcgctgcata | ccgtccggta ggtcggaag | cgtgcagtgc cgaggcggat | 240 |
| tcccgcattg | acagcgcgtg | cgttgcaagg caacaatgga | ctcaaatgtc tcggaatcgc | 300 |
| tgacgattcc | caggtttctc | cggcaagcat agcgcatggc | gtctccatgc gagaatgtcg | 360 |
| cgcttgccgg | ataaaagggg | agccgctatc ggaatggacg | caagccacgg ccgcagcagg | 420 |
| tgcggtcgag | ggcttccagc | cagttccagg gcagatgtgc | cggcagaccc tcccgctttg | 480 |
| ggggaggcgc | aagccgggtc | cattcggata gcatctcccc | atgcaaagtg ccggccaggg | 540 |
| caatgcccgg | agccggttcg | aatagtgacg gcagagagac | aatcaaatca tgagccaacc | 600 |
| atcttatggc | ccgctgttcg | aggccctggc ccactacaat | gacaagctgc tggccatggc | 660 |
| caaggcccag | acagagcgca | ccgcccaggc gctgctgcag | accaatctgg acgatctggg | 720 |
| ccaggtgctg | gagcagggca | gccagcaacc ctggcagctg | atccaggccc agatgaactg | 780 |
| gtggcaggat | cagctcaagc | tgatgcagca caccctgctc | aaaagcgcag gccagccgag | 840 |
| cgagccggtg | atcaccccgg | agcgcagcga tcgccgcttc | aaggccgagg cctggagcga | 900 |
| acaacccatc | tatgactacc | tcaagcagtc ctacctgctc | accgccaggc acctgctggc | 960 |
| ctcggtggat | gccctggagg | gcgtcccca gaagagccgg | gagcggctgc gtttcttcac | 1020 |
| ccgccagtac | gtctctgcca | tggccccag caacttcctg | gccaccaacc ccgagctgct | 1080 |
| caagctgacc | ctggagtccg | gcggccagaa cctggtgcgc | ggactggccc tcttggccga | 1140 |
| ggatctggag | cgcagcgccg | atcagctcaa catccgcctg | accgacgaat ccgccttcga | 1200 |
| gctcgggcgg | gatctggccc | tgaccccggg ccgggtggtg | cagcgcaccg agctctatga | 1260 |
| gctcattcag | tacagcccga | ctaccgagac ggtgggcaag | acacctgtgc tgatagtgcc | 1320 |
| gcccttcatc | aacaagtact | acatcatgga catgcggccc | cagaactccc tggtcgcctg | 1380 |
| gctggtcgcc | cagggccaga | cggtattcat gatctcctgg | cgcaacccgg gcgtggccca | 1440 |
| ggcccaaatc | gatctcgacg | actacgtggt ggatggcgtc | atcgccgccc tggacggcgt | 1500 |

```
ggaggcggcc accggcgagc gggaggtgca cggcatcggc tactgcatcg gcggcaccgc    1560
cctgtcgctc gccatgggct ggctggcggc gcggcgccag aagcagcggg tgcgcaccgc    1620
caccctgttc actaccctgc tggacttctc ccagcccggg gagcttggca tcttcatcca    1680
cgagcccatc atagcggcgc tcgaggcgca aaatgaggcc aagggcatca tggacgggcg    1740
ccagctggcg gtcagcttca gcctgctgcg ggagaacagc ctctactgga actactacat    1800
cgacagctac ctcaagggtc agagcccggt ggccttcgat ctgctgcact ggaacagcga    1860
cagcaccaat gtggcgggca agacccacaa cagcctgctg cgccgtctct acctggagaa    1920
ccagctggtg aagggggagc tcaagatccg caacacccgc atcgatctcg gcaaggtgaa    1980
gacccctgtg ctgctggtgt cggcggtgga cgatcacatc gccctctggc agggcacctg    2040
gcagggcatg aagctgtttg gcggggagca gcgcttcctc ctggcggagt ccggccacat    2100
cgccggcatc atcaacccgc cggccgccaa caagtacggc ttctggcaca acggggccga    2160
ggccgagagc ccggagagct ggctggcagg ggcgacgcac cagggcggct cctggtggcc    2220
cgagatgatg ggctttatcc agaaccgtga cgaagggtca gagcccgtcc ccgcgcgggt    2280
cccggaggaa gggctggccc ccgccccgg ccactatgtc aaggtgcggc tcaaccccgt    2340
gtttgcctgc ccaacagagg aggacgccgc atgacgcttg catgagtgcc ggcgtgcgtc    2400
atgcacggcg ccggcaggcc tgcaggttcc ctcccgtttc cattgaaagg actacacaat    2460
gactgacgtt gtcatcgtat ccgccgcccg caccgcggtc ggcaagtttg gcggctcgct    2520
ggccaagatc ccggcaccgg aactgggtgc cgtggtcatc aaggccgcgc tggagcgcgc    2580
cggcgtcaag ccggagcagg tgagcgaagt catcatgggc caggtgctga ccgccggttc    2640
gggccagaac cccgcacgcc aggccgcgat caaggccggc ctgccggcga tggtgccggc    2700
catgaccatc aacaaggtgt gcggctcggg cctgaaggcc gtgatgctgg ccgccaacgc    2760
gatcatggcg ggcgacgccg agatcgtggt ggccggcggc aggaaaaaca tgagcgccgc    2820
cccgcacgtg ctgccgggct cgcgcgatgg tttccgcatg ggcgatgcca agctggtcga    2880
caccatg                                                             2887
```

<210> SEQ ID NO 9
<211> LENGTH: 246
<212> TYPE: PRT
<213> ORGANISM: Artificial Sequence
<220> FEATURE:
<223> OTHER INFORMATION: acetocetyl-CoA reductase

<400> SEQUENCE: 9

```
Met Gln Ser Arg Val Ala Leu Val Thr Gly Gly Thr Gly Gly Ile Gly
1               5                   10                  15

Thr Ser Ile Ile Gln Arg Leu Ala Gln Thr Gly His Arg Val Ala Thr
            20                  25                  30

Asn Tyr Arg Asp Glu Asp Arg Ala Arg Ala Trp Gln Glu Lys Met Arg
        35                  40                  45

Ala Ala Gly Val Glu Val Ala Leu Ala Pro Gly Asp Val Ser Ser Pro
    50                  55                  60

Glu Gln Ala Gln Ala Leu Val Glu Gln Ile Gln Arg Asp Leu Gly Pro
65                  70                  75                  80

Ile Glu Val Leu Val Asn Asn Ala Gly Ile Thr Arg Asp Ser Thr Phe
                85                  90                  95

His Arg Met Thr Pro Leu Gln Trp Asn Glu Val Ile Gly Thr Asn Leu
            100                 105                 110
```

Asn Ser Cys Phe Asn Val Thr Arg Pro Val Ile Glu Gly Met Arg Glu
            115                 120                 125

Arg Lys Trp Gly Arg Ile Val Gln Ile Ser Ser Ile Asn Gly Leu Lys
130                 135                 140

Gly Gln Tyr Gly Gln Ala Asn Tyr Ala Ala Ala Lys Ala Gly Met His
145                 150                 155                 160

Gly Phe Thr Ile Ser Leu Ala Arg Glu Asn Ala Arg Phe Gly Val Thr
                165                 170                 175

Val Asn Thr Val Ser Pro Gly Tyr Val Ala Thr Asp Met Val Met Ser
            180                 185                 190

Val Pro Glu Glu Val Arg Ala Lys Ile Val Ala Glu Ile Pro Thr Gly
        195                 200                 205

Arg Leu Gly Thr Pro Asn Glu Ile Ala Tyr Ala Val Ser Phe Leu Val
    210                 215                 220

Ala Glu Glu Ala Ala Trp Ile Thr Gly Ser Asn Leu Asp Ile Asn Gly
225                 230                 235                 240

Gly His His Met Gly Trp
                245

<210> SEQ ID NO 10
<211> LENGTH: 246
<212> TYPE: PRT
<213> ORGANISM: Artificial Sequence
<220> FEATURE:
<223> OTHER INFORMATION: acetoacetyl-CoA reductase

<400> SEQUENCE: 10

Met Gln Lys Leu Ala Leu Ile Thr Gly Ser Lys Gly Gly Ile Gly Ser
1               5                   10                  15

Ala Ile Thr Glu Lys Leu Val Gln Asp Gly Phe Arg Ile Ile Ala Thr
            20                  25                  30

Tyr Phe Thr Gly Asn Tyr Glu Cys Ala Lys Glu Trp Phe Asp Glu Lys
        35                  40                  45

Gly Phe Ser Glu Asp Gln Val Thr Leu Phe Glu Leu Asp Val Thr Asp
    50                  55                  60

Ala Asp Ser Cys Arg Glu Arg Leu Thr Lys Leu Leu Glu Asn Glu Gly
65                  70                  75                  80

Thr Val Asp Val Leu Val Asn Asn Ala Gly Ile Thr Arg Asp Cys Thr
                85                  90                  95

Phe Lys Arg Met Thr Ala Glu Gln Trp Asn Asp Val Ile Asn Thr Asn
            100                 105                 110

Leu Asn Ser Val Phe Asn Val Thr Gln Pro Leu Phe Ala Ala Met Cys
        115                 120                 125

Glu Lys Gly Gly Arg Ile Ile Asn Ile Ser Ser Val Asn Gly Leu
    130                 135                 140

Lys Gly Gln Phe Gly Gln Thr Asn Tyr Ser Ala Ala Lys Ala Gly Met
145                 150                 155                 160

Ile Gly Phe Ser Lys Ala Leu Ala Phe Glu Gly Ala Arg Ser Gly Val
                165                 170                 175

Thr Val Asn Val Val Ala Pro Gly Tyr Thr Gly Thr Pro Met Val Gln
            180                 185                 190

Ala Ile Arg Gln Asp Val Leu Asp Ser Ile Ile Glu Thr Val Pro Met
        195                 200                 205

Lys Arg Leu Ala Thr Pro Glu Glu Ile Ala Ser Ala Val Ala Tyr Leu
    210                 215                 220

Ala Ser Asp Ala Gly Ala Tyr Ile Thr Gly Glu Thr Leu Ser Val Asn
225                 230                 235                 240

Gly Gly Leu Tyr Met Gln
                245

<210> SEQ ID NO 11
<211> LENGTH: 271
<212> TYPE: PRT
<213> ORGANISM: Artificial Sequence
<220> FEATURE:
<223> OTHER INFORMATION: acetoacetyl-CoA reductase

<400> SEQUENCE: 11

Met Thr Thr Ala Ala Glu Lys Arg Ala Ala Thr Asn Ser Gly Ser
1               5                   10                  15

Glu Pro Val Arg Glu Ala Val Pro Pro Leu Lys Gln Arg Ile Ala Phe
                20                  25                  30

Val Ser Gly Gly Met Gly Gly Ile Gly Ser Ala Val Cys Arg Arg Leu
            35                  40                  45

Val Arg Asn Gly Ala Arg Val Val Ala Gly Cys Leu Pro Gly Tyr Glu
        50                  55                  60

Lys Lys Asp Glu Trp Ile Ala Lys Met Arg Gly Glu Gly Leu Gln Val
65                  70                  75                  80

His Ala Ala Glu Gly Asp Val Asp Asp Tyr Glu Ser Cys Ala Asp Met
                85                  90                  95

Phe Tyr Gln Ile Gly Ser Val Ile Gly Pro Val Asp Ile Leu Val Asn
            100                 105                 110

Asn Ala Gly Ile Thr Arg Asp Gly Met Phe Lys Arg Met Ser Pro Ala
        115                 120                 125

Asp Trp Tyr Ala Val Ile Asn Thr Asn Leu Asn Ser Val Phe Asn Val
130                 135                 140

Thr Arg Gln Val Ile Glu Gly Met Met Glu Arg Gly Trp Gly Arg Ile
145                 150                 155                 160

Ile Asn Ile Ser Ser Val Asn Ala Leu Lys Gly Gln Phe Gly Gln Thr
                165                 170                 175

Asn Tyr Ser Ala Ala Lys Ala Gly Met His Gly Phe Ser Lys Ala Leu
            180                 185                 190

Ala Gln Glu Val Val Lys Lys Gly Val Thr Val Asn Thr Val Ser Pro
        195                 200                 205

Gly Tyr Val Glu Thr Asp Met Val Arg Ala Met Lys Pro Glu Val Leu
210                 215                 220

Gln Ser Ile Val Glu Gln Ile Pro Met Gly Arg Phe Ala Gln Pro Glu
225                 230                 235                 240

Glu Ile Ala Ser Leu Val Ala Tyr Leu Ala Ser Glu Glu Ala Gly Tyr
                245                 250                 255

Ile Thr Gly Ala Asn Ile Ser Ile Asn Gly Gly Leu His Met Val
            260                 265                 270

<210> SEQ ID NO 12
<211> LENGTH: 248
<212> TYPE: PRT
<213> ORGANISM: Artificial Sequence
<220> FEATURE:
<223> OTHER INFORMATION: acetoacetyl-CoA reductase

<400> SEQUENCE: 12

Met Ala Asn Gln Ala Pro Val Ala Trp Val Thr Gly Gly Thr Gly Gly
1               5                   10                  15

```
Ile Gly Thr Ala Ile Cys Arg Ser Leu Ala Asp Ala Gly Tyr Leu Val
                20                  25                  30

Val Ala Gly Tyr His Asn Pro Glu Lys Ala Lys Thr Trp Leu Ala Ser
            35                  40                  45

Gln Gln Ala Asp Gly Tyr Asn Asn Ile Ala Leu Ser Gly Val Asp Leu
 50                  55                  60

Ala Asp His Gln Ala Cys Leu Gln Gly Ala Gln Ile Gln Glu Gln
 65                  70                  75                  80

His Gly Pro Ile Ser Val Leu Val Asn Cys Ala Gly Ile Thr Arg Asp
                85                  90                  95

Gly Thr Met Lys Lys Met Ser Tyr Glu Gln Trp Tyr Glu Val Ile Asp
            100                 105                 110

Thr Asn Leu Asn Ser Val Phe Asn Thr Cys Arg Ser Val Ile Glu Met
                115                 120                 125

Met Leu Glu Asn Gly Tyr Gly Arg Ile Ile Asn Ile Ser Ser Ile Asn
130                 135                 140

Gly Arg Lys Gly Gln Phe Gly Gln Ala Asn Tyr Ala Ala Ala Lys Ala
145                 150                 155                 160

Gly Met His Gly Leu Thr Met Ser Leu Ala Gln Glu Thr Ala Thr Lys
                165                 170                 175

Gly Ile Thr Val Asn Thr Val Ser Pro Gly Tyr Ile Ala Thr Asp Met
            180                 185                 190

Ile Met Asn Ile Pro Glu Lys Val Arg Glu Ala Ile Arg Glu Thr Ile
                195                 200                 205

Pro Val Lys Arg Tyr Gly Thr Pro Glu Glu Ile Gly Arg Leu Val Thr
210                 215                 220

Phe Ile Ala Asp Lys Glu Ser Gly Phe Ile Thr Gly Ala Asn Phe Asp
225                 230                 235                 240

Ile Asn Gly Gly Gln Phe Met Gly
                245

<210> SEQ ID NO 13
<211> LENGTH: 246
<212> TYPE: PRT
<213> ORGANISM: Artificial Sequence
<220> FEATURE:
<223> OTHER INFORMATION: acetoacetyl-CoA reductase

<400> SEQUENCE: 13

Met Ser Arg Val Ala Leu Val Thr Gly Gly Met Gly Gly Leu Gly Glu
1               5                   10                  15

Ala Ile Cys Ile Lys Met Ala Ala Leu Gly Tyr Gln Val Val Thr Thr
                20                  25                  30

Tyr Ser Pro Gly Asn Lys Thr Trp Lys Glu Trp Leu Asp Ser Met Asn
            35                  40                  45

Lys Met Gly Phe Gly Phe Arg Ala Tyr Pro Cys Asp Val Ala Asp Tyr
 50                  55                  60

Asp Ser Ala Thr Ala Cys Val Ala Leu Ile Val Lys Glu Val Gly Pro
 65                  70                  75                  80

Val Asp Val Leu Val Asn Asn Ala Gly Ile Thr Arg Asp Met Thr Phe
                85                  90                  95

Lys Lys Met Asp Lys Ile Asn Trp Asp Ala Val Val Ala Thr Asn Leu
                100                 105                 110

Asp Ser Thr Phe Asn Met Thr Lys Gln Val Cys Asp Gly Met Leu Glu
            115                 120                 125
```

```
Arg Gly Trp Gly Arg Ile Val Asn Ile Ser Ser Val Asn Gly Gln Lys
            130                 135                 140

Gly Ala Phe Gly Gln Thr Asn Tyr Ser Ala Ala Lys Ala Gly Met His
145                 150                 155                 160

Gly Phe Thr Lys Ala Leu Ala Leu Glu Val Ala Arg Lys Gly Val Thr
                165                 170                 175

Val Asn Thr Ile Ser Pro Gly Tyr Ile Gly Thr Lys Met Val Met Ala
            180                 185                 190

Ile Pro Ser Asp Val Leu Glu Ser Lys Ile Ile Pro Gln Ile Pro Met
            195                 200                 205

Gly Arg Leu Gly Lys Pro Glu Glu Val Ala Gly Leu Val Ala Tyr Leu
            210                 215                 220

Ala Ser Asp Glu Ala Ala Phe Leu Thr Gly Ala Asn Ile Ala Ile Asn
225                 230                 235                 240

Gly Gly Gln His Met Ser
                245

<210> SEQ ID NO 14
<211> LENGTH: 247
<212> TYPE: PRT
<213> ORGANISM: Artificial Sequence
<220> FEATURE:
<223> OTHER INFORMATION: acetoacetyl-CoA reductase

<400> SEQUENCE: 14

Met Thr Gln Arg Ile Ala Ile Val Thr Gly Ala Asn Gly Gly Leu Gly
1               5                   10                  15

Glu Ser Met Cys Lys Ala Leu Ala Glu Gln Gly Arg Lys Val Val Gly
                20                  25                  30

Thr Phe Val Pro Gly His Asp Ala Ala Ala Ser Trp Gln Glu Glu
            35                  40                  45

Met Lys Gln Gln Gly Phe Asp Ile Thr Met Lys Ala Val Asp Val Ser
50                  55                  60

Asp Phe Asn Asp Cys Lys Arg Leu Leu Glu Glu Ile Glu Ser Ser Glu
65                  70                  75                  80

Gly Ser Val Asp Ile Leu Val Asn Asn Ala Gly Ile Thr Arg Asp Ala
                85                  90                  95

Pro Leu Lys Lys Met Gln Pro Glu Gln Trp Gln Ala Val Ile Gly Thr
            100                 105                 110

Asn Leu Asn Ser Met Phe Asn Met Ser Gln Pro Ile Phe Glu Ala Met
            115                 120                 125

Cys Asn Arg Gly Trp Gly Arg Ile Val Asn Ile Ser Ser Leu Asn Gly
            130                 135                 140

Glu Lys Gly Gln Phe Gly Gln Ala Asn Tyr Ser Ala Ala Lys Ala Gly
145                 150                 155                 160

Ile Tyr Gly Phe Thr Lys Ala Ile Ala Gln Glu Gly Ala Lys Lys Gly
                165                 170                 175

Val Thr Val Asn Ser Val Ser Pro Gly Tyr Ile Asp Thr Pro Met Val
            180                 185                 190

Arg Gln Val Pro Glu Asn Val Leu Asn Ser Ile Val Gly Gly Ile Pro
            195                 200                 205

Val Gly Arg Leu Gly Gln Pro Glu Glu Ile Ala Arg Ala Val Ser Phe
            210                 215                 220

Leu Thr Ala Asp Asp Ala Gly Phe Ile Thr Gly Thr Asn Ile Ser Val
225                 230                 235                 240
```

Asn Gly Gly Gln Tyr Met Ala
              245

<210> SEQ ID NO 15
<211> LENGTH: 246
<212> TYPE: PRT
<213> ORGANISM: Artificial Sequence
<220> FEATURE:
<223> OTHER INFORMATION: acetoacetyl-CoA reductase

<400> SEQUENCE: 15

Met Ser Gln Lys Ile Ala Leu Val Thr Gly Ala Met Gly Gly Leu Gly
1               5                   10                  15

Thr Ala Ile Cys Gln Ser Leu Ala Arg Asp Gly Met Lys Val Val Ala
            20                  25                  30

Asn Cys Leu Pro Gly Phe Asp Gln Lys Glu Gly Trp Leu Ala Ala Gln
        35                  40                  45

Arg Asp Leu Gly Phe Asn Phe Ile Ala Ala Glu Gly Asp Val Ser Asp
    50                  55                  60

Tyr Asp Ser Cys Ala Ala Met Val Ala Arg Ile Glu Ala Glu Val Gly
65                  70                  75                  80

Pro Val Asp Val Leu Val Asn Asn Ala Gly Ile Thr Arg Asp Lys Phe
                85                  90                  95

Phe Pro Lys Met Gln Lys Ala Gln Trp Asp Ala Val Ile Asn Thr Asn
            100                 105                 110

Leu Asn Ser Leu Phe Asn Val Thr His His Val Ser Ala Lys Met Ala
        115                 120                 125

Glu Arg Gly Trp Gly Arg Ile Ile Ser Ile Ser Ser Val Asn Gly Val
    130                 135                 140

Lys Gly Gln Ala Gly Gln Thr Asn Tyr Ser Ala Ala Lys Ala Gly Val
145                 150                 155                 160

Leu Gly Phe Thr Lys Ala Leu Ala Ala Glu Leu Ala Thr Lys Gly Val
                165                 170                 175

Thr Val Asn Ala Val Ala Pro Gly Tyr Val Gly Thr Glu Met Val Met
            180                 185                 190

Ala Ile Arg Asp Asp Ile Arg Gln Gly Ile Ile Asp Thr Ile Pro Met
        195                 200                 205

Gly Arg Leu Gly Arg Pro Asp Glu Ile Gly Asp Leu Cys Ala Tyr Leu
    210                 215                 220

Ala Ser Asp Lys Ala Ala Tyr Ile Thr Gly Ala Thr Ile Asn Ile Asn
225                 230                 235                 240

Gly Gly Leu His Met Cys
              245

<210> SEQ ID NO 16
<211> LENGTH: 593
<212> TYPE: PRT
<213> ORGANISM: Artificial Sequence
<220> FEATURE:
<223> OTHER INFORMATION: PHA polymerase

<400> SEQUENCE: 16

Met Ser Gln Pro Ser Tyr Gly Pro Leu Phe Glu Ala Leu Ala His Tyr
1               5                   10                  15

Asn Asp Lys Leu Leu Ala Met Ala Lys Ala Gln Thr Glu Arg Thr Ala
            20                  25                  30

Gln Ala Leu Leu Gln Thr Asn Leu Asp Asp Leu Gly Gln Val Leu Glu

```
                35                  40                  45
Gln Gly Ser Gln Gln Pro Trp Gln Leu Ile Gln Ala Gln Met Asn Trp
 50                  55                  60

Trp Gln Asp Gln Leu Lys Leu Met Gln His Thr Leu Leu Lys Ser Ala
 65                  70                  75                  80

Gly Gln Pro Ser Glu Pro Val Ile Thr Pro Glu Arg Ser Asp Arg Arg
                 85                  90                  95

Phe Lys Ala Glu Ala Trp Ser Glu Gln Pro Ile Tyr Asp Tyr Leu Lys
                100                 105                 110

Gln Ser Tyr Leu Leu Thr Ala Arg His Leu Leu Ala Ser Val Asp Ala
                115                 120                 125

Leu Glu Gly Val Pro Gln Lys Ser Arg Glu Arg Leu Arg Phe Phe Thr
                130                 135                 140

Arg Gln Tyr Val Ser Ala Met Ala Pro Ser Asn Phe Leu Ala Thr Asn
145                 150                 155                 160

Pro Glu Leu Leu Lys Leu Thr Leu Glu Ser Gly Gly Gln Asn Leu Val
                165                 170                 175

Arg Gly Leu Ala Leu Leu Ala Glu Asp Leu Glu Arg Ser Ala Asp Gln
                180                 185                 190

Leu Asn Ile Arg Leu Thr Asp Glu Ser Ala Phe Glu Leu Gly Arg Asp
                195                 200                 205

Leu Ala Leu Thr Pro Gly Arg Val Val Gln Arg Thr Glu Leu Tyr Glu
                210                 215                 220

Leu Ile Gln Tyr Ser Pro Thr Thr Glu Thr Val Gly Lys Thr Pro Val
225                 230                 235                 240

Leu Ile Val Pro Pro Phe Ile Asn Lys Tyr Tyr Ile Met Asp Met Arg
                245                 250                 255

Pro Gln Asn Ser Leu Val Ala Trp Leu Val Ala Gln Gly Gln Thr Val
                260                 265                 270

Phe Met Ile Ser Trp Arg Asn Pro Gly Val Ala Gln Ala Gln Ile Asp
                275                 280                 285

Leu Asp Asp Tyr Val Val Asp Gly Val Ile Ala Ala Leu Asp Gly Val
                290                 295                 300

Glu Ala Ala Thr Gly Glu Arg Glu Val His Gly Ile Gly Tyr Cys Ile
305                 310                 315                 320

Gly Gly Thr Ala Leu Ser Leu Ala Met Gly Trp Leu Ala Ala Arg Arg
                325                 330                 335

Gln Lys Gln Arg Val Arg Thr Ala Thr Leu Phe Thr Thr Leu Leu Asp
                340                 345                 350

Phe Ser Gln Pro Gly Glu Leu Gly Ile Phe Ile His Glu Pro Ile Ile
                355                 360                 365

Ala Ala Leu Glu Ala Gln Asn Glu Ala Lys Gly Ile Met Asp Gly Arg
                370                 375                 380

Gln Leu Ala Val Ser Phe Ser Leu Leu Arg Glu Asn Ser Leu Tyr Trp
385                 390                 395                 400

Asn Tyr Tyr Ile Asp Ser Tyr Leu Lys Gly Gln Ser Pro Val Ala Phe
                405                 410                 415

Asp Leu Leu His Trp Asn Ser Asp Ser Thr Asn Val Ala Gly Lys Thr
                420                 425                 430

His Asn Ser Leu Leu Arg Arg Leu Tyr Leu Glu Asn Gln Leu Val Lys
                435                 440                 445

Gly Glu Leu Lys Ile Arg Asn Thr Arg Ile Asp Leu Gly Lys Val Lys
                450                 455                 460
```

```
Thr Pro Val Leu Leu Val Ser Ala Val Asp Asp His Ile Ala Leu Trp
465                 470                 475                 480

Gln Gly Thr Trp Gln Gly Met Lys Leu Phe Gly Gly Glu Gln Arg Phe
            485                 490                 495

Leu Leu Ala Glu Ser Gly His Ile Ala Gly Ile Ile Asn Pro Pro Ala
        500                 505                 510

Ala Asn Lys Tyr Gly Phe Trp His Asn Gly Ala Glu Ala Glu Ser Pro
    515                 520                 525

Glu Ser Trp Leu Ala Gly Ala Thr His Gln Gly Gly Ser Trp Trp Pro
530                 535                 540

Glu Met Met Gly Phe Ile Gln Asn Arg Asp Glu Gly Ser Glu Pro Val
545                 550                 555                 560

Pro Ala Arg Val Pro Glu Glu Gly Leu Ala Pro Ala Pro Gly His Tyr
                565                 570                 575

Val Lys Val Arg Leu Asn Pro Val Phe Ala Cys Pro Thr Glu Glu Asp
                580                 585                 590

Ala

<210> SEQ ID NO 17
<211> LENGTH: 169
<212> TYPE: DNA
<213> ORGANISM: Artificial Sequence
<220> FEATURE:
<223> OTHER INFORMATION: promoter

<400> SEQUENCE: 17
atgcctccac accgctcgtc acatcctgtt gcgttcactg gaatcccagt atctaatttg      60
acctgcgagc aagctgtcac cggatgtgct ttccggtctg atgagtccgt gaggacgaaa    120
cagcctctac aaataatttt gtttaactga ctgaattcat gggacaagc                169

<210> SEQ ID NO 18
<211> LENGTH: 20
<212> TYPE: DNA
<213> ORGANISM: Artificial Sequence
<220> FEATURE:
<223> OTHER INFORMATION: pK-R primer

<400> SEQUENCE: 18
gcagacttgg ccgggtacca                                                  20

<210> SEQ ID NO 19
<211> LENGTH: 19
<212> TYPE: DNA
<213> ORGANISM: Artificial Sequence
<220> FEATURE:
<223> OTHER INFORMATION: pK-F primer

<400> SEQUENCE: 19
caccgctcgt cacatcctg                                                   19

<210> SEQ ID NO 20
<211> LENGTH: 40
<212> TYPE: DNA
<213> ORGANISM: Artificial Sequence
<220> FEATURE:
<223> OTHER INFORMATION: phaCH1-F primer

<400> SEQUENCE: 20
tggtacccgg ccaagtctgc gggcgtgccc atgatgtaga                            40
```

<210> SEQ ID NO 21
<211> LENGTH: 42
<212> TYPE: DNA
<213> ORGANISM: Artificial Sequence
<220> FEATURE:
<223> OTHER INFORMATION: phaCH1-R primer

<400> SEQUENCE: 21
tgagacccaa ggtctccatg atttgattgt ctctctgccg tc        42

<210> SEQ ID NO 22
<211> LENGTH: 38
<212> TYPE: DNA
<213> ORGANISM: Artificial Sequence
<220> FEATURE:
<223> OTHER INFORMATION: phaCH2-F primer

<400> SEQUENCE: 22
ggagaccttg ggtctcagtg acgcttgcat gagtgccg            38

<210> SEQ ID NO 23
<211> LENGTH: 39
<212> TYPE: DNA
<213> ORGANISM: Artificial Sequence
<220> FEATURE:
<223> OTHER INFORMATION: phaCH2-R

<400> SEQUENCE: 23
caggatgtga cgagcggtgc atggtgtcga ccagcttgg           39

<210> SEQ ID NO 24
<211> LENGTH: 11
<212> TYPE: DNA
<213> ORGANISM: Artificial Sequence
<220> FEATURE:
<223> OTHER INFORMATION: primer

<400> SEQUENCE: 24
gtgaagagac c                                          11

<210> SEQ ID NO 25
<211> LENGTH: 21
<212> TYPE: DNA
<213> ORGANISM: Artificial Sequence
<220> FEATURE:
<223> OTHER INFORMATION: FphaCH1-F primer

<400> SEQUENCE: 25
tggtctggct ggcggactga g                               21

<210> SEQ ID NO 26
<211> LENGTH: 21
<212> TYPE: DNA
<213> ORGANISM: Artificial Sequence
<220> FEATURE:
<223> OTHER INFORMATION: phaCH2-R primer

<400> SEQUENCE: 26
ggcgaactca tcctgcgcct c                               21

<210> SEQ ID NO 27
<211> LENGTH: 24
<212> TYPE: DNA
<213> ORGANISM: Artificial Sequence
<220> FEATURE:
<223> OTHER INFORMATION: pKCH-C R primer

```
<400> SEQUENCE: 27
catgatttga ttgtctctct gccg                                              24

<210> SEQ ID NO 28
<211> LENGTH: 20
<212> TYPE: DNA
<213> ORGANISM: Artificial Sequence
<220> FEATURE:
<223> OTHER INFORMATION: pKCH-C F primer

<400> SEQUENCE: 28
gtgacgcttg catgagtgcc                                                   20

<210> SEQ ID NO 29
<211> LENGTH: 39
<212> TYPE: DNA
<213> ORGANISM: Artificial Sequence
<220> FEATURE:
<223> OTHER INFORMATION: phaB F primer

<400> SEQUENCE: 29
agagagacaa tcaaatcatg actcagcgca ttgcgtatg                              39

<210> SEQ ID NO 30
<211> LENGTH: 40
<212> TYPE: DNA
<213> ORGANISM: Artificial Sequence
<220> FEATURE:
<223> OTHER INFORMATION: phaB R primer

<400> SEQUENCE: 30
ggcactcatg caagcgtcac tcagcccata tgcaggccgc                             40

<210> SEQ ID NO 31
<211> LENGTH: 37
<212> TYPE: DNA
<213> ORGANISM: Artificial Sequence
<220> FEATURE:
<223> OTHER INFORMATION: phaJ-H1 Fp primer

<400> SEQUENCE: 31
tggtacccgg ccaagtctgt tcgacggcgt cttcgtt                                37

<210> SEQ ID NO 32
<211> LENGTH: 38
<212> TYPE: DNA
<213> ORGANISM: Artificial Sequence
<220> FEATURE:
<223> OTHER INFORMATION: phaJ-H1 Rp primer

<400> SEQUENCE: 32
cgagcggtgt ggaggcatct attcagtcag ggatgcct                               38

<210> SEQ ID NO 33
<211> LENGTH: 62
<212> TYPE: DNA
<213> ORGANISM: Artificial Sequence
<220> FEATURE:
<223> OTHER INFORMATION: phaJ-H2 Fp primer

<400> SEQUENCE: 33
ctacaaataa ttttgtttaa ctgactgaat tcatgggaca agcatgaaga cctacgagaa       60
ca                                                                      62
```

```
<210> SEQ ID NO 34
<211> LENGTH: 41
<212> TYPE: DNA
<213> ORGANISM: Artificial Sequence
<220> FEATURE:
<223> OTHER INFORMATION: phaJ-H2 Rp primer

<400> SEQUENCE: 34
cttgaagacg aaagggcctc gtggcgcctt atggaaatca g          41

<210> SEQ ID NO 35
<211> LENGTH: 18
<212> TYPE: DNA
<213> ORGANISM: Artificial Sequence
<220> FEATURE:
<223> OTHER INFORMATION: phaJ Fp primer

<400> SEQUENCE: 35
atgcctccac accgctcg                                    18

<210> SEQ ID NO 36
<211> LENGTH: 26
<212> TYPE: DNA
<213> ORGANISM: Artificial Sequence
<220> FEATURE:
<223> OTHER INFORMATION: phaJ Rp primer

<400> SEQUENCE: 36
ttaaacaaaa ttatttgtag aggctg                           26
```

ENGINEERED MICROORGANISMS EXPRESSING ACETOACETYL-COA REDUCTASE VARIANTS AND METHODS FOR INCREASING PROPORTION OF 3-HYDROXYHEXANOIC ACID IN PHA

CROSS REFERENCE TO RELATED APPLICATIONS

This application is a national stage application filed under 35 U.S.C. § 371 of International Patent Application No. PCT/CN2022/101796, filed Jun. 28, 2022, which claims the benefit of CN202210353444.8 filed Apr. 6, 2022.

INCORPORATION OF MATERIAL OF ASCII TEXT SEQUENCE LISTING BY REFERENCE

The sequence listing submitted herewith as a text file named "CNKH-1041US_SUBSTITUTE_SEQUENCE_LISTING" created on Apr. 10, 2023, which is 37,000 bytes in size, is hereby incorporated by reference in its entirety.

TECHNICAL FIELD

The present invention relates to the technical field of microorganisms, specifically, to engineered microorganisms expressing acetoacetyl-CoA reductase variants and methods for increasing the proportion of 3-hydroxyhexanoic acid in PHA.

BACKGROUND ART

Polyhydroxyalkanoates (PHAs) are a class of polymers synthesized by microorganisms with renewable and degradable characteristics and multi-material properties, which have a wide range of applications in the fields of medicine, materials and environmental protection. PHAs are widely present in microbial cells, mainly acting as carbon sources and energy storage carriers. According to different monomer types and polymerization modes, PHAs have a series of material properties with diversity from hard and brittle hard plastic to soft elastomer. Polyhydroxy butyrate (PHB, or P(3HB)), one of the PHAs, is a bacterially produced complex biopolymer, as a thermoplastic, has mechanical and physical properties comparable to those of conventional plastics such as polystyrene. However, due to its highly crystalline nature, P(3HB) is more brittle and harder than most conventional plastics, to the extent that it is not practical as a substitute for commercial plastics. Therefore, it is necessary to produce a copolymer containing a combination of 3HB and longer chain monomers to achieve improvement in thermal and physical properties. Poly(3-hydroxy butyrate-co-3-hydroxyhexanoate) (P(3HB-co-3HHx)) is a hybrid chain-length copolymer that is more flexible than the P(3HB) homopolymer, where the 3HHx (3-hydroxyhexanoate) monomer fraction largely determines the properties of the polymer. P(3HB-co-3HHx) copolymers with a high 3HHx molar fraction (referred to as H ratio) can exhibit properties similar to those of common commercial plastics such as low density polyethylene (LDPE). Therefore, it is of great significance to increase the proportion of 3HHx in 3HB-co-3HHx produced by the microorganisms.

*Ralstonia eutropha* (also known as *Cupriavidus* necator) is an important model bacterium for the study of PHA synthesis and is the most studied strain for PHB production. *Ralstonia eutropha* can accumulate PHB when carbon is in excess and nitrogen is deficient, while PHB synthesis is compromised when other intracellular carbon sources are metabolized vigorously.

SUMMARY OF THE INVENTION

The purpose of the present invention is to provide an acetoacetyl-CoA reductase variant and its coding gene capable of increasing the proportion of 3-hydroxyhexanoic acid in PHA produced by microorganisms, and engineered microorganisms for PHA production.

Specifically, the present invention provides the following technical solutions:

In a first aspect, the present invention provides an acetoacetyl-CoA reductase variant with amino acid sequence as represented by any one of SEQ ID NOs. 9-15.

In a second aspect, the present invention provides gene variants encoding the acetoacetyl-CoA reductase with nucleotide sequences as represented by any one of SEQ ID NOs. 1-7.

The present invention demonstrates experimentally that each of the above gene variants is capable of significantly increasing the proportion of 3-hydroxyhexanoic acid in PHA produced by the strains.

In a third aspect, the present invention provides biological material containing the above gene variants, the biological material being an expression cassette, a vector or a host cell.

In some embodiments of the present invention, the expression cassette containing the gene variants described above is obtained by operably linking a promoter, the gene variant described above, and a terminator. Depending on the need of expression and the upstream and downstream sequences of the expression cassette, the expression cassette may also not contain a terminator or may contain other transcription and translation regulatory elements such as enhancers.

In some embodiments of the present invention, the vectors containing the gene variants described above are plasmid vectors, which include replication-competent vectors and non-replication-competent vectors. The vectors carrying the nucleic acid molecules described above are not limited to plasmid vectors, but may also be vectors such as phages, viruses, and the like.

In some embodiments of the present invention, cells of *Escherichia coli* and *Ralstonia eutropha* containing the above gene variants, expression cassettes or vectors are provided, but the type of host cells is not limited to this, and can be any microbial cells or animal cells that can be used for protein expression.

In a fourth aspect, the present invention provides use of an acetoacetyl-CoA reductase variant or its coding gene in increasing the proportion of 3-hydroxyhexanoic acid in PHA produced by engineered microorganisms, the acetoacetyl-CoA reductase variant having an amino acid sequence as represented by any one of SEQ ID NOs. 9-15.

Based on the amino acid sequences of the acetoacetyl-CoA reductase variants provided above and the codon rules, a person skilled in the art is able to obtain the sequences of genes encoding the acetoacetyl-CoA reductase variants described above. The sequences of genes encoding the same amino acid sequence are not unique, but all genes capable of encoding the acetoacetyl-CoA reductase variants described above are within the scope of protection of the present invention.

In some embodiments of the present invention, the nucleotide sequence of the coding gene is represented by any one of SEQ ID NOs. 1-7.

The above use can be achieved by any one or more of the following ways:
(1) introducing a plasmid comprising a gene encoding the acetoacetyl-CoA reductase variant:
(2) inserting one or more copies of the gene encoding the acetoacetyl-CoA reductase variant into the genome.

In some embodiments of the present invention, the genomic in situ phaB gene of the microorganism is not inactivated.

In some embodiments of the present invention, the genomic in situ phaB gene of the microorganism is retained intact.

In the above use, the engineered microorganism further includes one or more of the following modifications:
(1) expression of a PHA polymerase variant capable of synthesizing poly(3-hydroxy butyrate-co-3-hydroxyhexanoate);
(2) enhanced expression and/or enzyme activity of (R)-enoyl-CoA hydratase.

In some embodiments of the present invention, the PHA polymerase variant capable of synthesizing poly(3-hydroxy butyrate-co-3-hydroxyhexanoate) contains a mutation of asparagine to serine at position 149 and a mutation of aspartate to glycine at position 171 compared to the original PHA polymerase.

In some embodiments of the present invention, the amino acid sequence of the PHA polymerase variant is represented by SEQ ID NO. 16.

In some embodiments of the present invention, the enhanced expression and/or enzyme activity of (R)-enoyl-CoA hydratase is achieved by initiating the transcription of the gene encoding (R)-enoyl-CoA hydratase in the genome with the promoter represented by SEQ ID NO. 17.

In the above use, the microorganism is preferably *Ralstonia eutropha*, *E. coli* or *Halomonas*.

In some embodiments of the present invention, the increase in the proportion of 3-hydroxyhexanoic acid in PHA produced by the engineered microorganism is an increase in the proportion of 3-hydroxyhexanoic acid in PHA produced by the engineered microorganism using lipids as carbon sources.

In some embodiments of the present invention, the increase in the proportion of 3-hydroxyhexanoic acid in PHA produced by the engineered microorganism is an increase in the proportion of 3-hydroxyhexanoic acid in PHA produced by the engineered microorganism using vegetable oils as carbon sources.

The vegetable oils include a mixture selected from one or more of palm oil, peanut oil, soy bean oil, flax oil, rapeseed oil, castor oil, and corn oil. In a fifth aspect, the present invention provides the application of an acetoacetyl-CoA reductase variant or its coding gene or biological material containing the coding gene in the construction of microorganisms for the production of polyhydroxy fatty acid esters or their derivatives.

Based on the function that the acetoacetyl-CoA reductase variants provided by the present invention can increase the proportion of 3-hydroxyhexanoic acid in PHA produced by microorganisms, the genes encoding these variants and the biological materials containing these genes can be used in the construction of strains for the production of PHA.

In the above applications, the microorganisms are preferably *Ralstonia eutropha*, *E. coli* or *Halomonas*.

In some embodiments of the present invention, the gene represented by any one of SEQ ID NOs. 1-7 is introduced into *Ralstonia eutropha* to construct a PHA-producing strain.

In a sixth aspect, the present invention provides an engineered *Ralstonia eutropha*, which expresses the acetoacetyl-CoA reductase variant, the acetoacetyl-CoA reductase variant having an amino acid sequence as represented by any one of SEQ ID NOs. 9-15.

In the present invention, expression of the acetoacetyl-CoA reductase variant may be achieved by any one or more of the following methods:
(1) introducing a plasmid comprising a gene encoding the acetoacetyl-CoA reductase variant:
(2) inserting one or more copies of the gene encoding the acetoacetyl-CoA reductase variant into the genome.

In some embodiments of the present invention, the acetoacetyl-CoA reductase variant is expressed by inserting one copy of the gene encoding the acetoacetyl-CoA reductase variant into the genome.

In some embodiments of the present invention, the acetoacetyl-CoA reductase variant is inserted at the position where the phaC gene is located in the genome.

In some embodiments of the present invention, the gene encoding the acetoacetyl-CoA reductase variant is represented by any one of SEQ ID NOs. 1-7. The sequences of these coding genes are those capable of achieving efficient and correct expression of the acetoacetyl-CoA reductase variant in *Ralstonia eutropha* obtained according to the codon preference of *Ralstonia eutropha* and combined with manual optimization and screening, the use of which facilitates the acetoacetyl-CoA reductase variant to better function in *Ralstonia eutropha* to increase the proportion of 3-hydroxyhexanoic acid in PHA.

In some embodiments of the present invention, the genomic in situ phaB gene of the microorganism is not inactivated.

In some embodiments of the present invention, the genomic in situ phaB gene of the microorganism is retained intact.

In some embodiments of the present invention, in order to facilitate synthesis of poly(3-hydroxy butyrate-co-3-hydroxy hexanoate), the engineered *Ralstonia eutropha* further includes one or more of the following modifications:
(1) expression of a PHA polymerase variant capable of synthesizing poly(3-hydroxy butyrate-co-3-hydroxyhexanoate;
(2) enhanced expression and/or enzyme activity of (R)-enoyl-CoA hydratase.

Wherein, the PHA polymerase variant capable of synthesizing poly(3-hydroxy butyrate-co-3-hydroxyhexanoate) can be made by mutating the amino acid sequence of the bacterial PHA polymerase to enable it to polymerize C6 fatty acid (3-hydroxyhexanoic acid), either by using a prior art PHA polymerase variant capable of polymerizing C6 fatty acid (3-hydroxyhexanoic acid), or by combining the mutation sites of prior art PHA polymerase variants capable of polymerizing poly(3-hydroxy butyrate-co-3-hydroxyhexanoate) to obtain new and more efficient PHA polymerase variants.

In some embodiments of the present invention, the PHA polymerase variant capable of synthesizing poly(3-hydroxy butyrate-co-3-hydroxyhexanoate) contains a mutation of asparagine to serine at position 149 and a mutation of aspartic acid to glycine at position 171 compared to the original PHA polymerase.

In some embodiments of the present invention, the amino acid sequence of the PHA polymerase variant is represented by SEQ ID NO. 16.

The above expression of a PHA polymerase variant capable of synthesizing poly(3-hydroxy butyrate-co-3-hydroxyhexanoate) is achieved by any one or more of the following ways:

(1) introducing a plasmid including a gene encoding the PHA polymerase variant capable of synthesizing poly (3-hydroxy butyrate-co-3-hydroxyhexanoate;
(2) inserting one or more copies of the gene encoding a variant of the PHA polymerase capable of synthesizing poly(3-hydroxy butyrate-co-3-hydroxyhexanoate) into the genome.

In some embodiments of the present invention, a PHA polymerase variant capable of synthesizing poly(3-hydroxy butyrate-co-3-hydroxyhexanoate) is expressed while the original PHA polymerase encoding gene of the genome is inactivated.

In some embodiments of the present invention, the gene encoding the PHA polymerase variant capable of synthesizing poly(3-hydroxy butyrate-co-3-hydroxyhexanoate) is inserted into the genome.

In some embodiments of the present invention, an expression plasmid containing a gene encoding a PHA polymerase variant capable of synthesizing poly(3-hydroxy butyrate-co-3-hydroxyhexanoate) is introduced.

In some embodiments of the present invention, the expression plasmid is a stable expression plasmid and stable expression of the plasmid is achieved by carrying in the plasmid a synthetic gene for a metabolite essential for the growth of the strain while inactivating the synthetic gene in the genome.

In some embodiments of the present invention, the plasmid containing the gene encoding the PHA polymerase variant represented by SEQ ID NO. 16 further contains the proC gene and the genomic proC gene of the engineered *Ralstonia eutropha* is inactivated.

The above enhancement of expression of the enzyme may be achieved by any one or more of the following ways (1)-(4):

(1) introducing a vector containing a gene encoding the enzyme:
(2) increasing the copy number of the gene encoding the enzyme in the genome:
(3) altering the sequence of transcription and/or translation regulatory elements (including promoters, and the like) of a gene encoding the enzyme in the genome:
(4) altering the nucleotide sequence of the gene encoding the enzyme.

The enhancement of the enzyme activity may be achieved by substitution, deletion or insertion of one or more amino acids of the enzyme.

In some embodiments of the present invention, the enhanced expression and/or enzyme activity of (R)-enoyl-CoA hydratase is achieved by initiating the transcription of the gene encoding (R)-enoyl-CoA hydratase in the genome with the promoter represented by SEQ ID NO. 17.

In some embodiments of the present invention, initiation of transcription of the gene encoding (R)-enoyl-CoA hydratase in the genome is achieved by inserting the promoter represented by SEQ ID NO. 17 in the intergenic region of the gene encoding genomic (R)-enoyl-CoA hydratase and its upstream gene.

The expression of (R)-enoyl-CoA hydratase is silenced in wild-type *Ralstonia eutropha*, and in the present invention, the promoter used to enhance the expression of (R)-enoyl-CoA hydratase and enzyme activity, is not limited to the promoter represented by SEQ ID NO. 17; all DNA fragments that can function as promoters in *Ralstonia eutropha* are capable of initiating transcription of (R)-enoyl-CoA hydratase and enhancing the expression and/or enzyme activity of (R)-enoyl-CoA hydratase.

In some embodiments of the present invention, the enhanced expression and/or enzyme activity of (R)-enoyl-CoA hydratase is achieved by initiating the transcription of the gene encoding (R)-enoyl-CoA hydratase in the genome with the promoter upstream of the (R)-enoyl-CoA hydratase gene in strain BPS-050 of *Ralstonia eutropha*.

The present invention demonstrates by experimental validation that the acetoacetyl-CoA reductase encoding gene variant of the present invention that function to increase the proportion of 3-hydroxy hexanoic acid in PHA produced by engineered microorganisms is not depend on the specific promoter sequence of the (R)-enoyl-CoA hydratase gene, but only on the ability of (R)-enoyl-CoA hydratase to be expressed in engineered microorganisms.

In some embodiments of the present invention, the engineered *Ralstonia eutropha* is obtained by modification with wild-type *Ralstonia eutropha, Ralstonia eutropha* H16 or *Ralstonia eutropha* BPS-050 as the original strain.

Among them, *Ralstonia eutropha* BPS-050 has been deposited in China General Microbiological Culture Collection Center (CGMCC for short, Address: Building 3, NO. 1 Courtyard, West Beichen Road, Chaoyang District, Beijing, Institute of Microbiology, Chinese Academy of Sciences, postal code: 100101) on Oct. 13, 2021, with the taxonomic designation of *Ralstonia eutropha*, a deposit number of CGMCC No. 23600.

In a seventh aspect, the present invention provides a library of engineered *Ralstonia eutropha* transformants, the library of transformants including at least 2 strains of the engineered *Ralstonia eutropha* described above.

In some embodiments of the present invention, the engineered *Ralstonia eutropha* in the library of transformants expresses an acetoacetyl-CoA reductase variant as represented by any one of SEQ ID NOs. 9-15, and each strain of the engineered *Ralstonia eutropha* in the library of transformants expresses an acetoacetyl-CoA reductase variant with a different amino acid sequence.

In some embodiments of the present invention, the library of transformants includes 2, 3, 4, 5, 6 or 7 strains of the engineered *Ralstonia eutropha* described above.

In an eighth aspect, the present invention provides a method of constructing the engineered *Ralstonia eutropha*, the method includes the step of modifying the *Ralstonia eutropha* to express the acetoacetyl-CoA reductase variant.

In some embodiments of the present invention, in order to promote the ability of the *Ralstonia eutropha* to synthesize poly(3-hydroxy butyrate-co-3-engineered hydroxyhexanoate), the method further includes one or more of the following modifications to the *Ralstonia eutropha:*

(1) expression of a PHA polymerase variant capable of synthesizing poly(3-hydroxybutyrate-co-3-hydroxyhexanoate);
(2) enhanced expression and/or enzyme activity of (R)-enoyl-CoA hydratase.

In some embodiments of the present invention, the amino acid sequence of the PHA polymerase variant capable of synthesizing poly(3-hydroxy butyrate-co-3-hydroxyhexanoate) is represented by SEQ ID NO. 16.

In some embodiments of the present invention, the method includes initiating the transcription of the gene encoding the genomic (R)-enoyl-CoA hydratase with the promoter represented by SEQ ID NO. 17.

In some embodiments of the present invention, the method includes inserting into the genome the gene encoding the PHA polymerase variant capable of synthesizing poly(3-hydroxybutyrate-co-3-hydroxyhexanoate).

In some embodiments of the present invention, the method includes introducing a plasmid carrying the gene encoding the PHA polymerase variant capable of synthesizing poly(3-hydroxybutyrate-co-3-hydroxyhexanoate).

In some embodiments of the present invention, the method includes introducing a plasmid carrying the gene encoding the PHA polymerase variant capable of synthesizing poly(3-hydroxy butyrate-co-3-hydroxyhexanoate) and a proC gene, and inactivating the proC gene in the genome.

Wherein, gene inactivation can be achieved by gene knockout, silent expression, RNA interference and the like.

In a ninth aspect, the present invention provides any one of the following uses of the engineered *Ralstonia eutropha:*
(1) use in the fermentation production of polyhydroxy fatty acid esters or their derivatives: and
(2) use in breeding strains for the fermentation production of polyhydroxy fatty acid esters or their derivatives.

In the above use, the breeding of strains for fermentation production of polyhydroxy fatty acid esters or their derivatives may specifically be as follows: using the engineered *Ralstonia eutropha* provided by the present invention as the original strain, breeding the strains for fermentation production of polyhydroxy fatty acid esters or their derivatives by genetic engineering modification, mutagenesis or domestication methods.

In a tenth aspect, the present invention provides a method for fermentative production of polyhydroxy fatty acid esters or derivatives thereof, which includes the step of culturing the engineered *Ralstonia eutropha* and obtaining a culture.

In some embodiments of the present invention, the method includes the following steps: activating and culturing the engineered *Ralstonia eutropha*, inoculating the activated bacteria into a seed medium for seed culture to obtain a seed solution, and then inoculating the seed solution into a production medium to obtain the culture.

The medium commonly used for the culture of *Ralstonia eutropha* can be selected for the above culture. The medium may contain carbon source, nitrogen source and inorganic salt. Among them, the carbon source includes, but is not limited to, a combination of one or more of vegetable oils (e.g. palm oil), sucrose, glucose, molasses, maltose, fructose, and arabinose: the nitrogen source includes, but is not limited to, a combination of one or more of corn syrup, yeast extract, urea, ammonium sulfate, ammonium chloride, ammonium nitrate, and potassium nitrate: the inorganic salt includes, but is not limited to, phosphate, potassium salt, sodium salt, magnesium salt, zinc salt, iron salt, manganese salt, calcium salt, borate, cobalt salt, copper salt, nickel salt and molybdenum salt.

In some embodiments of the present invention, the method further includes the step of separating and extracting the culture obtained from the culture to collect the polyhydroxy fatty acid esters or their derivatives.

In an eleventh aspect, the present invention provides a method for increasing the proportion of 3-hydroxyhexanoic acid in PHA produced by an engineered microorganism, the method including: modifying a *Ralstonia eutropha* to express an acetoacetyl-CoA reductase variant, and the amino acid sequence of the acetoacetyl-CoA reductase variant is represented by any one of SEQ ID NOs. 9-15.

In the above methods, expression of the acetoacetyl-CoA reductase variant may be achieved by any one or more of the following methods:

(1) introducing a plasmid comprising a gene encoding the acetoacetyl-CoA reductase variant:
(2) inserting one or more copies of the gene encoding the acetoacetyl-CoA reductase variant into the genome.

In some embodiments of the present invention, the gene encoding the acetoacetyl-CoA reductase variant is represented by any one of SEQ ID NOs. 1-7.

In some embodiments of the present invention, the genomic in situ phaB gene of the microorganism is not inactivated.

In some embodiments of the present invention, the genomic in situ phaB gene of the microorganism is retained intact.

In the method described above, the engineered microorganism further includes one or more of the following modifications:

(1) expression of a PHA polymerase variant capable of synthesizing poly(3-hydroxybutyrate-co-3-hydroxyhexanoate);
(2) enhanced expression and/or enzyme activity of (R)-enoyl-CoA hydratase.

In some embodiments of the present invention, the PHA polymerase variant capable of synthesizing poly(3-hydroxybutyrate-co-3-hydroxyhexanoate) contains a mutation of asparagine to serine at position 149 and a mutation of aspartate to glycine at position 171 compared to the original PHA polymerase.

In some embodiments of the present invention, the amino acid sequence of the PHA polymerase variant is represented by SEQ ID NO. 16.

In some embodiments of the present invention, enhanced expression and/or enzyme activity of (R)-enoyl-CoA hydratase is achieved by initiating the transcription of the gene encoding the genome (R)-enoyl-CoA hydratase with the promoter represented by SEQ ID NO. 17.

In some embodiments of the present invention, the increase in the proportion of 3-hydroxyhexanoic acid in PHA produced by the engineered microorganism is an increase in the proportion of 3-hydroxyhexanoic acid in PHA produced by the engineered microorganism using lipids as carbon sources.

In some embodiments of the present invention, the increase in the proportion of 3-hydroxyhexanoic acid in PHA produced by the engineered microorganism is an increase in the proportion of 3-hydroxyhexanoic acid in PHA produced by the engineered microorganism using vegetable oils as carbon sources.

The vegetable oils include a mixture selected from one or more of palm oil, peanut oil, soybean oil, flax oil, rapeseed oil, castor oil, and corn oil.

In the present invention, the polyhydroxy fatty acid ester is preferably poly(3-hydroxy butyrate-co-3-hydroxyhexanoate); more preferably, poly(3-hydroxy butyrate-co-3-hydroxyhexanoate) with a high 3-hydroxyhexanoic acid ratio.

The beneficial effect of the present invention is that the acetoacetyl-CoA reductase variants and their coding genes provided by the present invention can significantly increase the proportion of 3-hydroxyhexanoic acid in PHA produced by the strain; and the proportion of 3-hydroxyhexanoic acid in PHA produced by the engineered *Ralstonia eutropha* constructed using the acetoacetyl-CoA reductase variants and their coding genes provided by the present invention is significantly increased, which provides new gene and strain resources for the development of engineered strains producing poly(3-hydroxy butyrate-co-3-hydroxyhexanoate) with high 3-hydroxycaproic acid ratio.

BRIEF DESCRIPTION OF THE DRAWINGS

In FIGS. 1, 2, 3, 4, 5 and 6, SEQ ID NO. 1, SEQ ID NO. 2, SEQ ID NO. 3, SEQ ID NO. 4, SEQ ID NO. 5, SEQ ID NO. 6 and SEQ ID NO. 7 represent the engineered *Ralstonia eutropha* expressing the genes encoding the acetoacetyl-CoA reductase variants with sequences as represented by SEQ ID NO. 1, SEQ ID NO. 2, SEQ ID NO. 3, SEQ ID NO. 4, SEQ ID NO. 5, SEQ ID NO. 6 and SEQ ID NO. 7, respectively.

SPECIFIC MODES FOR CARRYING OUT THE EMBODIMENTS

Figure 1:
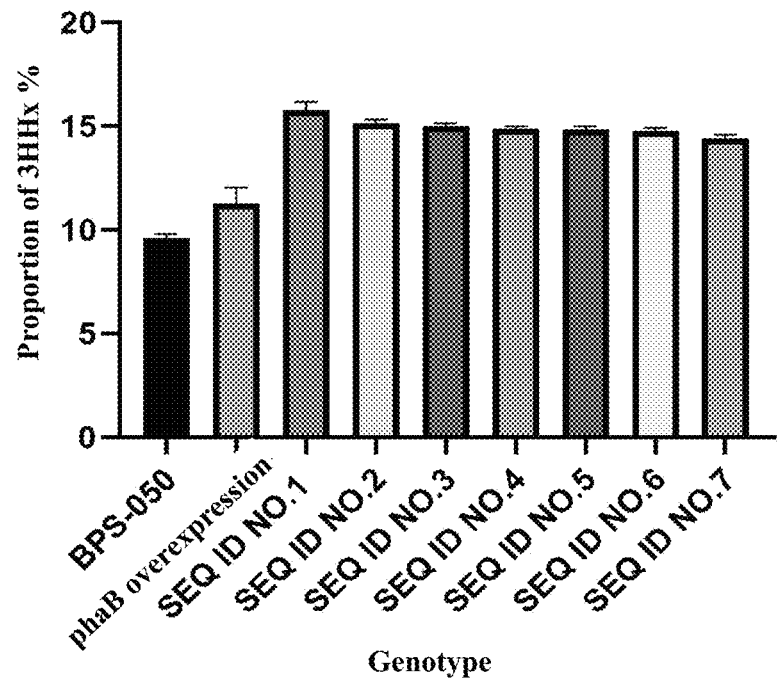
FIG. 1 shows the molar ratio of 3-hydroxyhexanoic acid in PHA produced by fermentation of each strain in Example 2 of the present invention.

The application of the present invention is not limited to the embodiments described or exemplified in the specification below: The present invention can be used in other embodiments and may be implemented or carried out in a variety of ways. In addition, the phrases and terms used herein are for descriptive purposes and should not be regarded as limiting. As used herein, the words "include", "comprise", or "have", "contain", "relate to" and variations thereof are intended to include the items enumerated below and their equivalents, as well as other items.

The specific embodiments provided by the present invention are based in part or in whole on the following findings: the present invention found the acetoacetyl-CoA reductase variants and their coding genes that can significantly increase the proportion of 3-hydroxyhexanoic acid in PHA produced by the strain. The genes encoding these acetoacetyl-CoA reductase variants can be introduced into strains having other genes required for the synthesis of PHA, in particular P(3HB-co-3HHx), which can be used to increase the proportion of 3-hydroxyhexanoic acid in PHA produced by these strains, thus obtaining engineered microorganisms. These engineered microorganisms can be used to produce PHA (particularly P(3HB-co-3HHx)), which in turn improves the ability of existing PHA fermentation strains to produce P(3HB-co-3HHx) with high 3-hydroxycaproic acid ratio. Based on the expression of the acetoacetyl-CoA reductase variant provided by the present invention, other modifications can be made to the engineered microorganisms, and the present invention found that the expression of the acetoacetyl-CoA reductase variant can be at least co-modified with the expression of the PHA polymerase (phaC) variant and the enhanced expression of phaJ, so as to further improve the yield of P(3HB-co-3HHx) with high 3-hydroxycaproic acid ratio.

In some embodiments, the present invention provides an acetoacetyl-CoA reductase variant having the amino acid sequence represented by any one of SEQ ID NOs. 9-15. These variants are capable of significantly increasing the proportion of 3-hydroxyhexanoic acid in PHA produced by the strain.

In some embodiments, the present invention provides a gene encoding the acetoacetyl-CoA reductase variant having the nucleotide sequence represented by any one of SEQ ID NOs. 1-7. These genes are optimized for expression in *Ralstonia eutropha*.

In some embodiments, the present invention provides an engineered *Ralstonia eutropha* that expresses the coding gene of acetoacetyl-CoA reductase variant.

In some embodiments, the present invention provides an engineered *Ralstonia eutropha* with the gene encoding the acetoacetyl-CoA reductase variant described above inserted into the genome.

In some embodiments, the present invention provides an engineered *Ralstonia eutropha* with the gene encoding the acetoacetyl-CoA reductase variant described above is inserted into the genome of *Ralstonia eutropha* BPS-050. These engineered *Ralstonia eutropha* produced a significantly higher proportion of 3-hydroxyhexanoic acid in P(3HB-co-3HHx) compared to *Ralstonia eutropha* BPS-050.

In some embodiments, the present invention provides an engineered *Ralstonia eutropha* with the gene encoding the acetoacetyl-CoA reductase variant described above inserted at the phaC gene in the genome of *Ralstonia eutropha* BPS-050.

In some embodiments, the present invention provides an engineered *Ralstonia eutropha* with the phaC gene in the genome of *Ralstonia eutropha* H16 replaced with a gene encoding a PHA polymerase variant (sequence as represented by SEQ ID NO. 16) and with the gene encoding the acetoacetyl-CoA reductase variant described above inserted into their genome. These engineered *Ralstonia eutropha* produced a significantly higher proportion of 3-hydroxyhexanoic acid in P(3HB-co-3HHx).

In some embodiments, the present invention provides an engineered *Ralstonia eutropha* with the promoter upstream of the phaJ4b gene of the genome of *Ralstonia eutropha* BPS-050 replaced with the promoter represented by SEQ ID NO. 17 and with the gene encoding the acetoacetyl-CoA reductase variant described above inserted into their genome. These engineered *Ralstonia eutropha* produced a significantly higher proportion of 3-hydroxyhexanoic acid in P(3HB-co-3HHx).

The following Examples are used to illustrate the present invention, but are not intended to limit the scope of the invention.

The experimental methods used in the following Examples are conventional if not otherwise specified.

The materials, reagents and the like used in the following Examples are commercially available if not otherwise specified. The enzyme reagents used were purchased from New England Biolabs (NEB) Co., Ltd., the kits for plasmid extraction were purchased from TIANGEN Biotech (Beijing) Co., Ltd., and the kits for DNA fragment recovery were purchased from Omega, USA. The corresponding operation steps were strictly in accordance with the product instructions. All culture mediums were prepared with deionized water unless otherwise specified.

The medium formulations used in the following Examples are as follows:

Seed medium I: 10 g/L peptone, 5 g/L Yeast Extract and 3 g/L glucose.

Seed medium II: 0.15% palm oil, 10 g/L peptone and 5 g/L Yeast Extract.

Production medium: 1.0% palm oil, 9.85 g/L $Na_2HPO_4 \cdot 12H_2O$, 1.5 g/L $KH_2PO_4$, 3.0 g/L $NH_4Cl$, 10 mL/L trace element solution I and 1 mL/L trace element solution II. Wherein, the composition of trace element solution I includes 20 g/L $MgSO_4$ and 2 g/L $CaCl_2$). The composition of trace element solution II includes 100 mg/L $ZnSO_4 \cdot 7H_2O$, 30 mg/L $MnCl_2 \cdot 4H_2O$, 300 mg/L $H_3BO_3$, 200 mg/L $CoCl_2 \cdot 6H_2O$, 10 mg/L $CuSO4.5H_2O$, 20 mg/L $NiCl_2 \cdot 6H_2O$ and 30 mg/L $NaMoO_4 \cdot 2H_2O$. The above reagents were all purchased from Sinopharm Chemical Reagent Co., Ltd.

Example 1: Construction of a Library of Transformants Expressing Acetoacetyl-CoA Reductase Variants Using BPS-050 as an Original Bacterium In the present Example, *Ralstonia eutropha* BPS-050 was used as an original bacterium, and the original bacterium was modified to express different acetoacetyl-CoA reductase variants respectively, which specifically included the following steps:

Step 1: Construction of Basic Plasmids

PCR amplification was performed using the genome of *Ralstonia eutropha* as a template to obtain the phaC upstream and downstream homologous fragments phaC-H1 and phaC-H2, and the BsaI sites were added to the posterior and anterior ends of phaC-H1 and phaC-H2 to facilitate subsequent operations: the modified plasmid pK18mob (Orita, I., Iwazawa, et al. J. Biosci. Bioeng. 113, 63-69) was used as a template for PCR amplification to obtain the vector fragment: phaC-H1 and phaC-H2 were ligated to the vector fragment by Gibson Assembly method to obtain the recombinant plasmid pKO-C. The primers used were shown in Table 1.

TABLE 1

| Primer name | Primer sequence (5'-3') |
|---|---|
| pK-R | gcagacttggccgggtacca (SEQ ID NO: 18) |
| pK-F | caccgctcgtcacatcctg (SEQ ID NO: 19) |
| phaCH1-F | tggtacccggccaagtctgc gggcgtgcccatgatgtaga (SEQ ID NO: 20) |
| phaCH1-R | tgagacccaaggtctccatg atttgattgtctctctgccg tc (SEQ ID NO: 21) |
| phaCH2-F | ggagaccttgggtctcagtg acgcttgcatgagtgccg (SEQ ID NO: 22) |
| phaCH2-R | caggatgtgacgagcggtgc atggtgtcgaccagcttgg (SEQ ID NO: 23) |

Step 2: Gene Synthesis

The sequences of the genes encoding different acetoacetyl-CoA reductase variants were optimized separately to make them well expressed in *Ralstonia eutropha*, and the optimized gene sequences encoding the acetoacetyl-CoA reductase variants are represented by SEQ ID NOs. 1-7.

When the above optimized genes encoding the acetoacetyl-CoA reductase variants were sent to synthesis, GGTCTCATC was added upstream of the DNA sequence and GTGAAGAGACC (SEQ ID NO: 24) was added downstream to facilitate the subsequent operation.

Step 3: Construction of a Target Strain Containing a Target Gene

The plasmid pKO-C constructed in step 1 was assembled with the plasmid containing the optimized gene encoding the acetoacetyl-CoA reductase variant returned by the gene synthesis company using Goldengate to obtain recombinant plasmids pKO-C-N carrying different genes encoding acetoacetyl-CoA reductase variants, respectively (N stands for the loaded gene encoding the acetoacetyl-CoA reductase variant). Each plasmid was transferred into *E. coli* S17-1 and then into *Ralstonia eutropha* BPS-050 by conjugative transfer, and positive clones were screened with LB plates containing both 500 μg/mL spectinomycin and 100 μg/mL apramycin, taking advantage of the inability of the suicide plasmids to replicate in the host bacteria. The recombinant plasmids with homologous fragments in the positive clone were integrated at the specific positions in the genome where H1 and H2 are located, resulting in the first homologous recombinant bacterium.

The first homologous recombinant bacterium was cultured on LB plates containing 100 mg/mL sucrose, and from these monoclonal clones, those without spectinomycin resistance were screened and PCR was performed using primers FphaCH1-F: tggtctggctggcggactgag (SEQ ID NO: 25) and phaCH2-R: ggcgaactcatcctgcgcctc (SEQ ID NO: 26). The recombinant bacteria inserted with the target gene were identified by sequencing, and the recombinant bacteria obtained were the stable plasmid version of *Ralstonia eutropha* ReAproCAphaC::N, with N being the inserted gene.

Step 4: Construction of Recombinant Bacteria Overexpressing the Original phaB Gene of *Ralstonia eutropha*

Referring to the method for constructing recombinant plasmids in step 3, recombinant plasmids containing the original phaB gene of *Ralstonia eutropha* were constructed using Gibson assembly as follows:

PCR amplification was performed using the plasmid obtained in step 1 as a template to obtain the plasmid backbone fragment. The phaB gene fragment was obtained by amplification using the genome of *Ralstonia eutropha* BPS-050 as a template. The above two fragments were ligated by Gibson Assembly method to obtain the recombinant plasmid pKO-C-phaB. The primers used are shown in Table 2.

TABLE 2

| Primer name | Primer sequence (5'-3') |
|---|---|
| pKCH-CR | CATGATTTGATTGTCT CTCTGCCG (SEQ ID NO: 27) |
| pKCH-CF | GTGACGCTTGCATGAG TGCC (SEQ ID NO: 28) |

TABLE 2-continued

| Primer name | Primer sequence (5'-3') |
|---|---|
| phaB F | AGAGAGACAATCAAAT CATGACTCAGCGCATT GCGTATG (SEQ ID NO: 29) |
| phaB R | GGCACTCATGCAAGCG TCACTCAGCCCATATG CAGGCCGC (SEQ ID NO: 30) |

The pKO-C-phaB plasmid was transferred into *E. coli* S17-1, and the recombinant bacterium was constructed with reference to the method in step 3 above, resulting in the overexpression strain ReAphaC::phaB that integrates the phaB gene at the phaC gene of the genome of *Ralstonia eutropha*, abbreviated as phaB overexpression.

Example 2: Fermentation Performance Test of Strains (1)

The fermentation performance of each strain expressing different acetoacetyl-CoA reductase variants was tested using *Ralstonia eutropha* BPS-050 and overexpression strain ReAphaC::phaB as control bacteria.

First, each strain (1000 μL) constructed in Example 1 preserved in glycerol tube was inoculated in seed medium I (20 mL) for 12 h of primary seed culture; then, 1% of seed medium I was inoculated in seed medium II for secondary seed culture; then 10 v/v % of seed medium II was inoculated into a 2 L small-scale fermentor (T&J Bioengineering Co. Ltd.) filled with 1.1 L production culture medium at 10 v/v %. The operating conditions were 30° C., stirring speed of 800 rpm, aeration rate of 1 L/min, and pH control between 6.7 and 6.8. 28% ammonia solution was used for pH control. Palm oil was continuously used as a carbon source during the incubation, and the incubation time was 54 hours.

The fermentation broth was taken for centrifugation to obtain the bacteria. The bacteria were dried to a constant weight. The weight of the dried bacteria was measured and recorded as dry weight. 100 mL of chloroform was added to the resulting dried bacteria, followed by stirring at room temperature overnight to extract polyester from the bacteria. The bacterial residue was filtered off and concentrated in an evaporator to a total volume of about 30 mL, then about 90 mL of hexane was slowly added and left for 1 hour with slow stirring. The precipitated polyester was filtered out and dried under vacuum at 5CTC for 3 hours. The mass of the dried polyester was measured and the polyester content in the bacterium was calculated.

Figure 2:
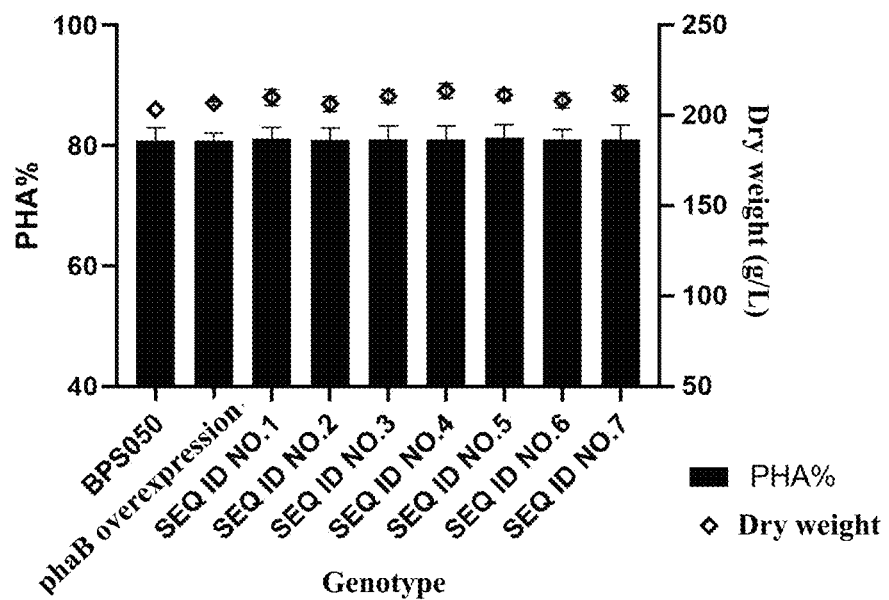
FIG. 2 shows the capacity of each strain in Example 2 of the present invention to produce PHA by fermentation.

The results showed that the proportion of PHA of each strain expressing different acetoacetyl-CoA reductase variants was not lower than that of the control bacteria, and the H ratio in PHA produced by each strain expressing different acetoacetyl-CoA reductase variants was significantly higher compared with the control bacteria. The H ratio in PHA produced by each strain is shown in FIG. 1, and the corresponding dry weights and PHA ratios are shown in FIG. 2.

Example 3: Construction of a Library of Transformants Expressing Acetoacetyl-CoA Reductase Variants Using BPS-050 as an Original Bacterium and the Fermentation Performance Test Thereof In the present Example, BPS-050 was used as an original bacterium, and the upstream promoter of phaJ4b gene was replaced with phaJ194 (SEQ ID NO.17), and the gene encoding the acetoacetyl-CoA reductase variant (SEQ ID NOs. 1-7) was expressed in it.

Step 1: Replacement of the Promoter Upstream of the phaJ4b Gene of BPS-050 by Homologous Recombination (1) PCR amplification was performed using the genome of *Ralstonia eutropha* BPS-050 as a template, and the upstream homologous fragment H1 of the phaJ gene promoter was obtained using phaJ-H1 Fp and phaJ-H1 Rp; the upstream homologous fragment H2 of the phaJ gene promoter was obtained using phaJ-H2 Fp and phaJ-H2 Rp.

(2) Gene synthesis of phaJ194 (SEQ ID NO.17), which is the promoter of phaJ gene (3) H1 and H2 obtained by PCR and the promoter phaJ194 were ligated with the vector fragment by Gibson Assembly method to obtain the recombinant plasmid pK18mob-phaJ194. The primers used are shown in Table 3.

TABLE 3

| Primer name | Primer sequence (5'-3') |
|---|---|
| phaJ-H1 Fp | TGGTACCCGGCCAAGTCTG TTCGACGGCGTCTTCGTT (SEQ ID NO: 31) |
| phaJ-H1 Rp | CGAGCGGTGTGGAGGCATC TATTCAGTCAGGGATGCCT (SEQ ID NO: 32) |
| phaJ-H2 Fp | CTACAAATAATTTTGTTTA ACTGACTGAATTCATGGGA CAAGCATGAAGACCTACGA GAACA (SEQ ID NO: 33) |
| phaJ-H2 Rp | CTTGAAGACGAAAGGGCCT CGTGGCGCCTTATGGAAAT CAG (SEQ ID NO: 34) |
| phaJ Fp | ATGCCTCCACACCGCTCG (SEQ ID NO: 35) |
| phaJ Rp | TTAAACAAAATTATTTGT AGAGGCTG (SEQ ID NO: 36) |

(4) The recombinant plasmid pK18mob-pha/194 was transferred into *E. coli* S17-1 and then into the original bacterium by conjugative transfer, and positive clones were screened with LB plates containing both 200 μg/mL kanamycin and 100 μg/mL apramycin, taking advantage of the inability of the suicide plasmid to replicate in the host bacterium. The recombinant plasmids with homologous fragments in the positive clone were integrated at the specific positions in the genome where H1 and H2 are located, resulting in the first homologous recombinant bacterium.

The first homologous recombinant bacterium was cultured on LB plates containing 100 mg/mL sucrose by scratching monoclonal clones, and from these monoclonal clones, clones without kanamycin resistance were screened and identified by PCR with primers phaJ Fp and phaJ Rp to obtain the recombinant bacterium of the corresponding fragment size, which is *Ralstonia eutropha* ReΔphaC::phaCac_phaJ194, abbreviated as Re_phaJ194.

Step 2: Different genes (SEQ ID NOs. 1-7) encoding acetoacetyl-CoA reductase variants were inserted into the genome of *Ralstonia eutropha* ReΔphaC::phaCac_phaJ194, respectively, by the method referring to Example 1.

Step 3: In *Ralstonia eutropha* ReΔphaC::phaCac_phaJ194, the original phaB gene of *Ralstonia eutropha* was overexpressed to obtain the phaB overexpression strain phaB overexpression-2.

Figure 3:
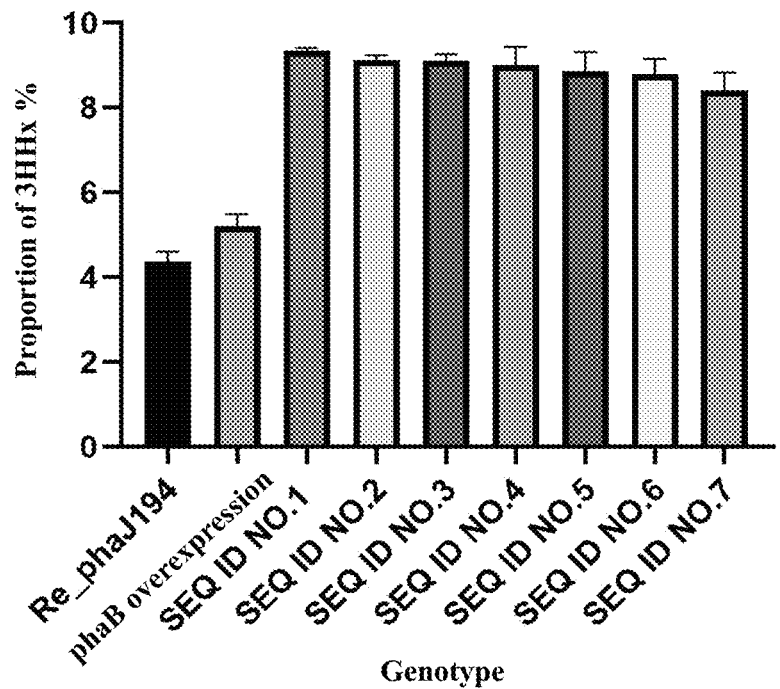
FIG. 3 shows the molar ratio of 3-hydroxyhexanoic acid in PHA produced by fermentation of each strain in Example 3 of the present invention.
Figure 4:
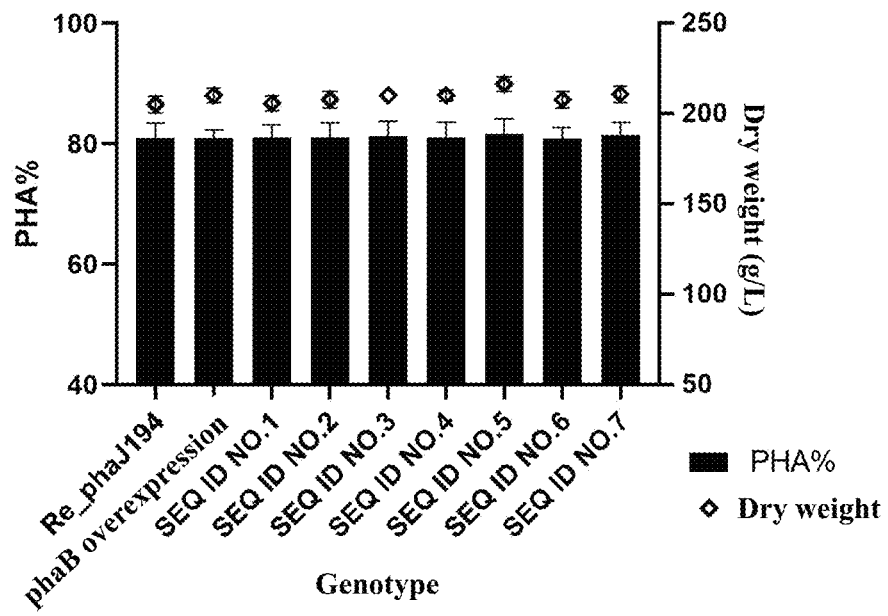
FIG. 4 shows the ability of each strain in Example 3 of the present invention to produce PHA by fermentation.

Step 4: The strains constructed in steps 2 and 3 were subjected to fermentation culture and PHA detection according to the method of Example 2. The results showed that the PHA proportion of each strain expressing different acetoacetyl-CoA reductase variants was not lower than that of the control bacteria, and the H ratio in the PHA produced by each strain expressing different acetoacetyl-CoA reductase variants was significantly higher compared with the control bacteria, and the H ratio in the PHA produced by each strain is shown in FIG. 3, and the corresponding dry weights and PHA ratios thereof are shown in FIG. 4.

Example 4: Construction of a Library of Transformants Expressing Acetoacetyl-CoA Reductase Variants Using H16 as an Original Bacterium and the Fermentation Performance Test Thereof In the present Example, *Ralstonia eutropha* H16 was used as an original bacterium, the genomic phaC gene of H16 was mutated to a phaC gene variant (the sequence of the encoded protein is represented by SEQ ID NO. 16), which enabled the recombinant bacteria to acquire the ability to synthesize 3HHx and express the genes encoding the acetoacetyl-CoA reductase variants (SEQ ID NOs. 1-7) in the obtained recombinant bacteria.

Step 1: Replacement of the phaC Gene in the Genome of *Ralstonia eutropha*

The sequence represented by SEQ ID NO. 8 was obtained by gene synthesis, the sequence carries approximately 600 bp upstream and downstream of the phaC gene and the phaC gene variant. Plasmid construction was performed by using the plasmids constructed in step 1 of Example 1, GGTCTCATC was added upstream and GTGAAGAGACC was added downstream of the DNA sequence during gene synthesis. A recombinant plasmid pK18mob-ΔphaC::phaCac was obtained by ligating the synthesized gene to the vector fragment via the Goldengate method.

The recombinant plasmid pK18mob-ΔphaC::phaCac was transferred into *E. coli* S17-1 and then into *Ralstonia eutropha* by conjugative transfer method, and positive clones were screened with LB plates containing both 200 μg/mL kanamycin and 100 μg/mL apramycin, taking advantage of the inability of the suicide plasmids to replicate in the host bacteria. The recombinant plasmids with homologous fragments in the positive clone were integrated into the genome at the specific locations where H1 and H2 are located, resulting in the first homologous recombinant bacterium.

The first homologous recombinant bacterium was cultured on LB plates containing 100 mg/mL sucrose by scratching monoclonal clones, and from these monoclonal clones, clones without kanamycin resistance were screened and PCR was performed with primers phaC-H1 FP and phaC-H2 RP, and the recombinant bacterium with phaC gene substitution was sequenced to identify the recombinant bacterium, which was obtained as *Ralstonia eutropha* ReΔphaC::phaCac, abbreviated as Re_H16.

Step 2: Different genes (SEQ ID NOs. 1-7) encoding acetoacetyl-CoA reductase variants were inserted into the genome of the *Ralstonia eutropha* ReΔphaC::phaCac constructed in step 1, respectively, by the method referring to Example 1.

Step 3: In *Ralstonia eutropha* ReΔphaC::phaCac constructed in step 1, the original phaB gene of *Ralstonia eutropha* H16 was overexpressed to obtain the phaB overexpression strain phaB overexpression-3.

Figure 5:
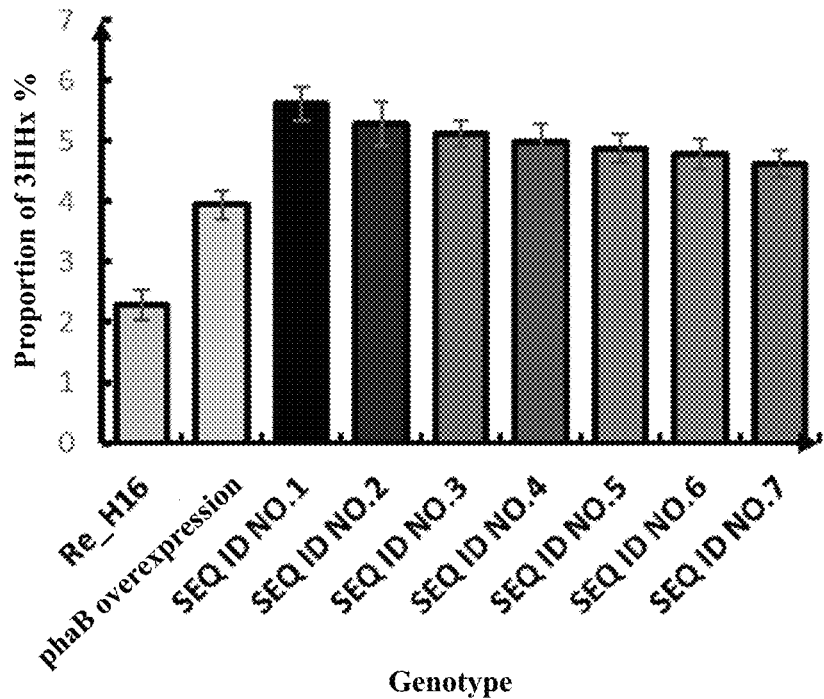
FIG. 5 shows the molar ratio of 3-hydroxyhexanoic acid in PHA produced by fermentation of each strain in Example 4 of the present invention.
Figure 6:
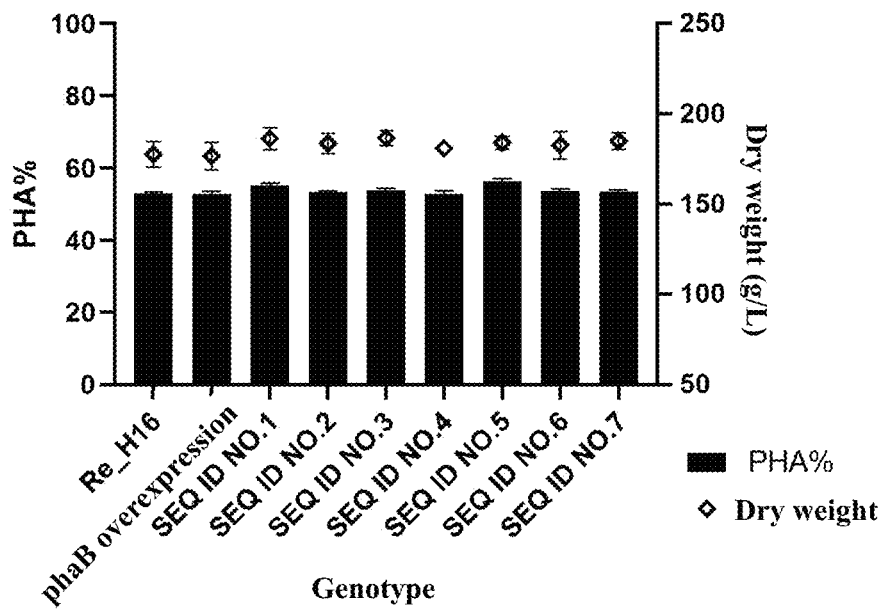
FIG. 6 shows the ability of each strain in Example 4 of the present invention to produce PHA by fermentation.

Step 4: The strains constructed in steps 2 and 3 were subjected to fermentation culture and PHA detection according to the method of Example 2. The results showed that the PHA proportion of each strain expressing different acetoacetyl-CoA reductase variants was not lower than that of the control bacteria, and the H ratio in the PHA produced by each strain expressing different acetoacetyl-CoA reductase variants was significantly higher compared with the control bacteria, and the H ratio in the PHA produced by each strain is shown in FIG. 5, and the corresponding dry weights and PHA ratios thereof are shown in FIG. 6.

Example 5: Fermentation Performance Test of Strains (2)

The strains constructed in Examples 1, 3 and 4 above were subjected to fermentation experiments using other vegetable oils as carbon sources, i.e., the carbon sources in their corresponding methods of fermentation test were replaced from palm oil to soybean oil and flax oil, respectively, and the fermentation performance tests were conducted for each strain constructed in Examples 1, 3 and 4. The results showed that the H ratio in PHA production and the ratio of cell dry weight to PHA for each strain when soy bean oil or flax oil was used as the carbon source tended to be consistent with the results of the fermentation performance tests performed with palm oil as the carbon source, showing no significant differences.

Although, the present invention has been described in detail above with a general description and specific embodiments, some modifications or improvements can be made on the basis of the present invention, as will be apparent to a person skilled in the art. Therefore, these modifications or improvements made without departing from the spirit of the present invention are within the scope of protection claimed by the present invention.

INDUSTRIAL APPLICABILITY

The present invention provides engineered microorganisms expressing acetoacetyl-CoA reductase variants and their coding genes, uses of the acetoacetyl-CoA reductase variants and their coding genes in increasing the proportion of 3-hydroxyhexanoic acid in PHA produced by microorganisms, and methods for increasing the proportion of 3-hydroxyhexanoic acid in PHA produced by microorganisms. By expressing the acetoacetyl-CoA reductase variant in microorganisms, the proportion of 3-hydroxyhexanoic acid in PHA synthesized by microorganisms is significantly increased, and at the same time, a high content of PHA in microbial cells can be ensured. The acetoacetyl-CoA reductase variants, their coding genes and the engineered microorganisms provided by the present invention provide new genes and strain resources for the development of the strains producing PHA with high proportion of 3-hydroxyhexanoic acid, and have important economic value and application prospects for the production of PHA with high proportion of 3-hydroxyhexanoic acid.

What is claimed is:

1. An engineered *Ralstonia eutropha* strain, wherein the engineered *Ralstonia eutropha* strain expresses an acetoacetyl-CoA reductase variant, the acetoacetyl-CoA reductase variant having the amino acid sequence of SEQ ID NO. 10.

2. The engineered *Ralstonia eutropha* strain according to claim 1, wherein the expression of the acetoacetyl-CoA reductase variant is achieved by any one or more of the following ways:
   (1) introducing a plasmid comprising a gene encoding the acetoacetyl-CoA reductase variant; and
   (2) inserting one or more copies of the gene encoding the acetoacetyl-CoA reductase variant into a genome of the engineered *Ralstonia eutropha* strain.

3. The engineered *Ralstonia eutropha* strain according to claim 2, wherein the gene encoding the acetoacetyl-CoA reductase variant is SEQ ID NO. 2.

4. The engineered *Ralstonia eutropha* strain according to claim 1, wherein the engineered *Ralstonia eutropha* strain further comprises one or more of the following modifications:
   (1) expression of a polyhydroxyalkanoate polymerase variant having the amino acid sequence of SEQ ID NO. 16, capable of synthesizing poly(3-hydroxybutyrate-co-3-hydroxyhexanoate); and
   (2) enhanced expression and/or enzyme activity of (R)-enoyl-CoA hydratase, wherein the enhanced expression and/or enzyme activity of the (R)-enoyl-CoA hydratase is achieved by initiating transcription of a gene encoding (R)-enoyl-CoA hydratase in the genome with the promoter of SEQ ID NO. 17.

5. A method for constructing the engineered *Ralstonia eutropha* strain according to claim 1, wherein the method comprises a step of modifying the *Ralstonia eutropha* strain to express the acetoacetyl-CoA reductase variant.

6. A method for constructing the engineered *Ralstonia eutropha* strain according to claim 2, wherein the method comprises a step of modifying the *Ralstonia eutropha* strain to express the acetoacetyl-CoA reductase variant.

7. A method for constructing the engineered *Ralstonia eutropha* strain according to claim 3, wherein the method comprises a step of modifying the *Ralstonia eutropha* strain to express the acetoacetyl-CoA reductase variant.

8. A method for constructing the engineered *Ralstonia eutropha* strain according to claim 7, wherein the method comprises a step of modifying the *Ralstonia eutropha* strain to express the acetoacetyl-CoA reductase variant.

9. The engineered *Ralstonia eutropha* strain according to claim 2, wherein the engineered *Ralstonia eutropha* strain further comprises one or more of the following modifications:
   (1) expression of a polyhydroxyalkanoate polymerase variant having the amino acid sequence of SEQ ID NO. 16, capable of synthesizing poly(3-hydroxybutyrate-co-3-hydroxyhexanoate); and
   (2) enhanced expression and/or enzyme activity of (R)-enoyl-CoA hydratase, wherein the enhanced expression and/or enzyme activity of the (R)-enoyl-CoA hydratase is achieved by initiating transcription of a gene encoding (R)-enoyl-CoA hydratase in a genome of the engineered *Ralstonia eutropha* strain with the promoter of SEQ ID NO. 17.

10. The engineered *Ralstonia eutropha* strain according to claim 3, wherein the engineered *Ralstonia eutropha* strain further comprises one or more of the following modifications:

(1) expression of a polyhydroxyalkanoate polymerase variant having the amino acid sequence of SEQ ID NO. 16, capable of synthesizing poly(3-hydroxybutyrate-co-3-hydroxyhexanoate); and (2) enhanced expression and/or enzyme activity of (R)-enoyl-CoA hydratase, wherein the enhanced expression and/or enzyme activity of the (R)-enoyl-CoA hydratase is achieved by initiating transcription of a gene encoding (R)-enoyl-CoA hydratase in a genome of the engineered *Ralstonia eutropha* strain with the promoter of SEQ ID NO. 17.

11. A method for constructing the engineered *Ralstonia eutropha* strain according to claim 9, wherein the method comprises a step of modifying the *Ralstonia eutropha* strain to express the acetoacetyl-CoA reductase variant.

12. A method for constructing the engineered *Ralstonia eutropha* strain according to claim 10, wherein the method comprises a step of modifying the *Ralstonia eutropha* strain to express the acetoacetyl-CoA reductase variant.

* * * * *